US010668147B2

(12) United States Patent
Stein et al.

(10) Patent No.: US 10,668,147 B2
(45) Date of Patent: Jun. 2, 2020

(54) ANTI-CD89 CYTOTOXIC COMPLEX

(71) Applicants: Fraunhofer-Gesellschaft zur Foerderung der angewandten Forschung e.V., Munich (DE); Rheinisch-Westfaelische Technische Hochschule Aachen, Aachen (DE)

(72) Inventors: Christoph Stein, Darmstadt (DE); Radoslav Mladenov, Zurich (CH); Bernhard Stockmeyer, Erlangen (DE); Stefan Barth, Capetown (ZA); Lea Christin Schenke, Holzgerlingen (DE); Rainer Fischer, Aachen (DE)

(73) Assignees: FRAUNHOFER-GESELLSCHAFT ZUR FOERDERUNG DER ANGEWANDTEN FORSCHUNG E.V., Munich (DE); RHEINISCH-WESTFAELISCHE TECHNISCHE HOCHSCHULE AACHEN, Aachen (DE)

( * ) Notice: Subject to any disclaimer, the term of this patent is extended or adjusted under 35 U.S.C. 154(b) by 29 days.

(21) Appl. No.: 15/560,770

(22) PCT Filed: Mar. 25, 2015

(86) PCT No.: PCT/EP2015/056386
§ 371 (c)(1),
(2) Date: Sep. 22, 2017

(87) PCT Pub. No.: WO2016/150496
PCT Pub. Date: Sep. 29, 2016

(65) Prior Publication Data
US 2018/0050102 A1 Feb. 22, 2018

(51) Int. Cl.
| *A61K 39/395* | (2006.01) |
| *G01N 33/566* | (2006.01) |
| *G01N 33/574* | (2006.01) |
| *A61K 47/68* | (2017.01) |
| *C07K 16/28* | (2006.01) |

(52) U.S. Cl.
CPC ........ *A61K 39/395* (2013.01); *A61K 47/6809* (2017.08); *A61K 47/6849* (2017.08); *C07K 16/28* (2013.01); *G01N 33/566* (2013.01); *G01N 33/574* (2013.01); *C07K 2317/74* (2013.01)

(58) Field of Classification Search
CPC .................................... A61K 39/395
USPC ..................................... 424/130.1
See application file for complete search history.

(56) References Cited

U.S. PATENT DOCUMENTS

| 4,946,778 A | 8/1990 | Ladner et al. | |
| 2003/0082643 A1* | 5/2003 | Hudson .............. | C07K 16/283 435/7.21 |

FOREIGN PATENT DOCUMENTS

| EP | 2 465 536 A1 | 6/2012 |
| WO | 2007/104743 A1 | 9/2007 |

OTHER PUBLICATIONS

Singh et al (Mol Cancer Ther, 2007, 6(2): 562-569).*
PCT/EP2015/056386 International Search Report and Written Opinion dated Nov. 4, 2015.
Albo et al. "Kinetics and Immunophenotypic Characterization of Circulating Hematopoietic Progenitor Cells After Peripheral Blood Stem Cell Transplantation," Haematolgica, 2004, 89:845-591.
Barth et al. "Ki4(scFc)-ETA', A New Recombinant Anti-CD30 Immunotoxin with Highly Specific Cytotoxic Activity Against Disseminated Hodgkin Tumors in SCID Mice," Blood, Jun. 15, 2000, 95(12): 3909-3914.
Becker et al. "Antibody-Based Immunotoxins for the Treatment of Cancer," Antibodies, 2012, 1:39-69.
Berges et al. "Human Cytolytic Fusion Proteins: Modified Versions of Human Granzyme B and Angiogenin Have the Potential to Replace Bacterial Toxins in Targeted Therapies Against CD64+ Diseases," Antibodies, 2014, 3:92-115.
Dunphy et al. "The Value of CD-64 Expression in Distinguishing Acute Myeloid Leukemia with Monocytic Differentiation from Other Subtypes of Acute Myeloid Leukemia: A Flow Cytometric Analysis of 64 Cases," Archives of Pathology and Laboratory Medicine, 2007, 131:748-754.
Gasiorowski et al. "Antibody Therapy for Acute Myeloid Leukaemia," British Journal of Haematology, 2013, 164:481-495.
Guettinger et al. "A Recombinant Bispecific Single-Chain Fragment Variable Specific for HLA Class II and Fc-alpha-RI (CD89) Recruits Polymorphonuclear Neutrophils for Efficient Lysis of Malignant B Lymphoid Cells," The Journal of Immunology, Dec. 30, 2009, 184(3)1210-1217.
Hamre et al. "Expression and Modulation of the Human Immunoglobulin A Fc Receptor (CD89) and the FcR gamma Chain on Myeloid Cells in Blood Tissue," Scandinavian Journal of Immunology, 2003, 57:506-516.
Huhn et al. "Human Angiogenin Fused to Human CD30 Ligand (Ang-CD30L) Exhibits Specific Cytotoxicity against CD30-Positive Lymphoma," Cancer Research, Dec. 15, 2001, 61(24):8737-8742.

(Continued)

*Primary Examiner* — Sean E Aeder
(74) *Attorney, Agent, or Firm* — Wagenknecht IP Law Group PC

(57) ABSTRACT

Complexes suitable for targeting and killing a human target cell comprising a first polypeptide with a binding structure for binding the complex to the cellular surface receptor CD89 (e.g. with an anti CD89 antibody) presented on the cell surface of the human target cell and a second polypeptide comprising a toxic effector domain, preferably *Pseudomonas* exotoxin A); to nucleic acid molecules encoding said complexes, vectors, host cells containing the nucleic acids and methods for preparation and producing such complexes; compositions and methods for using said complexes for the treatment of diseases, in particular of cancer diseases like leukemia.

20 Claims, 12 Drawing Sheets

Specification includes a Sequence Listing.

(56) References Cited

OTHER PUBLICATIONS

Hristodorov et al. "Macrophage-Targeted Therapy: CD64-Based Immunotoxins for Treatment of Chronic Inflammatory Diseases," 2012, Toxins, 4:676-694.
Hristodorov et al. "Microtubule-associated Protein Tau Facilitates the Targeted Killing of Proliferating Cancer Cells in Vitro and in a Xenograft Mouse Tumour Model in Vivo," British Journal of Cancer, 2013, 109(6):1570-1578.
Klausz et al. "The Novel Multispecies Fc-Specific Pseudomonas Exotoxin A Fusion Protein alpha-Fc-ETA' Enables Screening of Antibodies for Immunotoxin Development," Journal of Immunological Methods, Feb. 2015, 418:75-83.
Krauss et al. "Targeting Malignant B-Cell Lymphoma with a Humanized Anti-CD22 scFv-Angiogenin Immunoenzyme," British Journal of Haematology, Feb. 21, 2005, 128(5):602-609.
Monnier et al. "In Vivo Applications of Single Chain Fv (Variable Domain) (scFv) Fragments," Antibodies, 2013, 2:193-208.
Morton et al. "CD89: the Human Myeloid IgA Fc Receptor," Archivum Immunologiae et Therapiae Experimentalis, 2001, 49:217-229.
Schiffer et al. Species-Dependent Functionality of the Human Cytolytic Fusion Proteins Granzyme B-H22(scFv) and H22(scFv)-Angiogenin in Macrophages, Antibodies, 2013, 2(1):9-18.
Schiffer et al. "Targeted ex vivo Reduction of CD64-positive Monocytes in Chronic Myelomonocytic Leukemia and Acute Myelomonicytic Leukemia Using Human Granzyme B-based Cytolytic Fusion Proteins," International Journal of Cancer, 2014, 135:1497-1508.
Schwemmlein et a;. "A CD33-specific Single-Chain Immunotoxin Mediates Potent Apoptosis of Cultured Human Myeloid Leukaemia Cells," British Journal of Haematology, 2006, 133:141-151.
Stahnke et al. "Granzyme B-H22(scFv), a Human Immunotoxin Targeting CD64 in Acute Myeloid Leukemia of Monocytic Subtypes," Molecular Cancer Therapy, 2008, 7(9)2924-2932.
Stein et al. "Novel Conjugates of Single-Chain Fv Antibody Fragments Specific for Stem Cell Antigen CD123 Mediate Potent Death of Acute Myeloid Leukaemia Cells," British Journal of Haemotology, 148:879-889.
Thorpe et al. "Clonal Analysis of a Human Antimouse Antibody (HAMA) Response," Scandinavian Journal of Immunology, 2003, 57:85-92.
Tur et al. "Recombinant CD64-Specific Single Chain Immunotoxin Exhibits Specific Ctyotoxicity Against Acute Myeloid Leukemia Cells," Cancer Research, Dec. 1, 2003, 63:8414-8419.

* cited by examiner

Figure 11

SEQ ID NO: 1 CD89(scFv)

MADYKDVVMTQTPLTLSITIGQPASISCKSSQSLLDSDGKTYLNWLLQRPGQS
PTRLIYLVSKLDSGVPDRFTGSGSGTDFTLKISRVEAEDLGIYYCWQGAHFPQ
TFGGGTKLELKRGGGGSGGGGSGGGGSGGGGSEVQLQQTGPELVKPGASVKIS
CKASGYSFTDYIIFWVKQSHGKSLEWTGNINPYYGSTSYNLKFKGKATLTVDK
SSSTAYMQLNSLTSXDSAVYYCVRGVYYYGSSYEAFPYWGQGTLVTVS

SEQ ID NO: 2 CD89(scFv)-ETA'

MAQPAMADYKDVVMTQTPLTLSITIGQPASISCKSSQSLLDSDGKTYLNWLL
QRPGQSPTRLIYLVSKLDSGVPDRFTGSGSGTDFTLKISRVEAEDLGIYYCWQ
GAHFPQTFGGGTKLELKRGGGGSGGGGSGGGGSGGGGSEVQLQQTGPELVKP
GASVKISCKASGYSFTDYIIFWVKQSHGKSLEWTGNINPYYGSTSYNLKFKGK
ATLTVDKSSSTAYMQLNSLTSXDSAVYYCVRGVYYYGSSYEAFPYWGQGTLVT
VSAAAELASGGPEGGSLAALTAHQACHLPLETFTRHRQPRGWEQLEQCGYPV
QRLVALYLAARLSWNQVDQVIRNALASPGSGDLGEAIREQPEQARLALTLA
AAESERFVRQGTGNDEAGAANADVVSLTCPVAAGECAGPADSGDALLERNYP
TGAEFLGDGGDVSFSTRGTQNWTVERLLQAHRQLEERGYVFVGYHGTFLEAA
QSIVFGGVRARSQDLDAIWRGFYIAGDPALAYAYAQDQEPDARGRIRNGALLR
VYVPRSSLPGFYRTSLTLAAPEAAGEVERLIGHPLPLRLDAITGPEEEGGRLET
ILGWPLAERTVVIPSAIPTDPRNVGGDLDPSSIPDKEQAISALPDYASQPGKPP
REDLK

SEQ ID NO: 3 EGbR201K (granzyme B mutant)-CD89(scFv)

DDDDKIIGGHEAKPHSRPYMAFLMIWDQKSLKRCGGFLIRDDFVLTAAHCWG
SSINVTLGAHNIKEQEPTQQFIPVKRAIPHPAYNPKNFSNDIMetLLQLERKAK
RTRAVQPLRLPSNKAQVKPGQTCSVAGWGQTAPLGKHSHTLQEVKMTVQED
RKCESDLRHYYDSTIELCVGDPEIKKTSFKGDSGGPLVCNKVAQGIVSYGKNN
GMPPRACTKVSSFVHWIKKTMKRYAEHEGDAAQPAMADYKDVVMTQTPLTL
SITIGQPASISCKSSQSLLDSDGKTYLNWLLQRPGQSPTRLIYLVSKLDSGVPD
RFTGSGSGTDFTLKISRVEAEDLGIYYCWQGAHFPQTFGGGTKLELKRGGGGS
GGGGSGGGGSEVQLQQTGPELVKPGASVKISCKASGYSFTDYIIFWVK
QSHGKSLEWTGNINPYYGSTSYNLKFKGKATLTVDKSSSTAYMQLNSLTSXDS
AVYYCVRGVYYYGSSYEAFPYWGQGTLVTVSA

Figure 12

SEQ ID NO: 4 CD89(scFv)-Ang GGRR (angiogenin mutant)

MTQTPLTLSITIGQPASISCKSSQSLLDSDGKTYLNWLLQRPGQSPTRLIYLVS
KLDSGVPDRFTGSGSGTDFTLKISRVEAEDLGIYYCWQGAHFPQTFGGGTKLE
LKRGGGGSGGGGSGGGGSGGGGSEVQLQQTGPELVKPGASVKISCKASGYSFT
DYIIFWVKQSHGKSLEWTGNINPYYGSTSYNLKFKGKATLTVDKSSSTAYMQ
LNSLTSXDSAVYYCVRGVYYYGSSYEAFPYWGQGTLVTVSAAALESRQDNSRY
THFLTQHYDAKPQGRDDRYCESIMRRRGLTSPCKDINTFIHGNKRSIKAICEN
KNGNPHRENLRISKSSFQVTTCKLHRRSPWPPCQYRATAGFRNVVVACENGL
PVHLDQSIFRRP

SEQ ID NO: 5 CD89(scFv)-MAPtau

DVVMTQTPLTLSITIGQPASISCKSSQSLLDSDGKTYLNWLLQRPGQSPTRLIY
LVSKLDSGVPDRFTGSGSGTDFTLKISRVEAEDLGIYYCWQGAHFPQTFGGGT
KLELKRGGGGSGGGGSGGGGSGGGGSEVQLQQTGPELVKPGASVKISCKASGY
SFTDYIIFWVKQSHGKSLEWTGNINPYYGSTSYNLKFKGKATLTVDKSSSTAY
MQLNSLTSXDSAVYYCVRGVYYYGSSYEAFPYWGQGTLVTVSAAAMAEPRQE
FEVMEDHAGTYGLGDRKDQGGYTMHQDQEGDTDAGLKAEAGIGDTPSLEDE
AAGHVTQARMVSKSKDGTGSDDKKAKGADGKTKIATPRGAAPPGQKGQANA
TRIPAKTPPAPKTPPSSGEPPKSGDRSGYSSPGSPGTPGSRSRTPALPTPPTRE
PKKVAVVRTPPKSPSSAKSRLQTAPVPMDLKNVKSKIGATENLKHQPGGGK
VQIINKKLDLSNVQSKCGSKDNIKHVPGGGSVQIVYKPVDLSKVTSKCGSLGNI
HHKPGGGQVEVKSEKLDFKDRVQSKIGSLDNITHVPGGGNKKIETHKLTFRE
NAKAKTDHGAEIVYKSPVVSGDTSPRHLSNVSSTGSIDMVDSPQLATLADEVS
ASLAKQGLPKKKRKV

SEQ ID NO: 6 CD89/FCAR (uniprot ID: P24071)

QEGDFPMPFISAKSSPVIPLDGSVKIQCQAIREAYLTQLMIIKNSTYREIGRRL
KFWNETDPEFVIDHMDANKAGRYQCQYRIGHYRFRYSDTLELVVTGLYGKPF
LSADRGLVLMPGENISLTCSSAHIPFDRFSLAKEGELSLPQHQSGEHPANFSL
GPVDLNVSGIYRCYGWYNRSPYLWSFPSNALELVVTDSIHQDYTTQN

SEQUENCE LISTING

```
<160> NUMBER OF SEQ ID NOS: 6

<210> SEQ ID NO 1
<211> LENGTH: 260
<212> TYPE: PRT
<213> ORGANISM: Artificial Sequence
<220> FEATURE:
<223> OTHER INFORMATION: CD89(scFv)
<220> FEATURE:
<221> NAME/KEY: misc_feature
<222> LOCATION: (227)..(227)
<223> OTHER INFORMATION: Xaa can be any naturally occurring amino acid

<400> SEQUENCE: 1

Met Ala Asp Tyr Lys Asp Val Val Met Thr Gln Thr Pro Leu Thr Leu
1               5                   10                  15

Ser Ile Thr Ile Gly Gln Pro Ala Ser Ile Ser Cys Lys Ser Ser Gln
            20                  25                  30

Ser Leu Leu Asp Ser Asp Gly Lys Thr Tyr Leu Asn Trp Leu Leu Gln
        35                  40                  45

Arg Pro Gly Gln Ser Pro Thr Arg Leu Ile Tyr Leu Val Ser Lys Leu
    50                  55                  60

Asp Ser Gly Val Pro Asp Arg Phe Thr Gly Ser Gly Ser Gly Thr Asp
65                  70                  75                  80

Phe Thr Leu Lys Ile Ser Arg Val Glu Ala Glu Asp Leu Gly Ile Tyr
```

-continued

```
                    85                  90                  95
Tyr Cys Trp Gln Gly Ala His Phe Pro Gln Thr Phe Gly Gly Thr
                100                 105                 110
Lys Leu Glu Leu Lys Arg Gly Gly Gly Ser Gly Gly Gly Gly Ser
                115                 120                 125
Gly Gly Gly Gly Ser Gly Gly Gly Ser Glu Val Gln Leu Gln Gln
            130                 135                 140
Thr Gly Pro Glu Leu Val Lys Pro Gly Ala Ser Val Lys Ile Ser Cys
145                 150                 155                 160
Lys Ala Ser Gly Tyr Ser Phe Thr Asp Tyr Ile Ile Phe Trp Val Lys
                165                 170                 175
Gln Ser His Gly Lys Ser Leu Glu Trp Thr Gly Asn Ile Asn Pro Tyr
            180                 185                 190
Tyr Gly Ser Thr Ser Tyr Asn Leu Lys Phe Lys Gly Lys Ala Thr Leu
                195                 200                 205
Thr Val Asp Lys Ser Ser Thr Ala Tyr Met Gln Leu Asn Ser Leu
                210                 215                 220
Thr Ser Xaa Asp Ser Ala Val Tyr Tyr Cys Val Arg Gly Val Tyr Tyr
225                 230                 235                 240
Tyr Gly Ser Ser Tyr Glu Ala Phe Pro Tyr Trp Gly Gln Gly Thr Leu
                245                 250                 255
Val Thr Val Ser
            260
```

<210> SEQ ID NO 2
<211> LENGTH: 637
<212> TYPE: PRT
<213> ORGANISM: Artificial Sequence
<220> FEATURE:
<223> OTHER INFORMATION: CD89(scFv)-ETA'
<220> FEATURE:
<221> NAME/KEY: misc_feature
<222> LOCATION: (232)..(232)
<223> OTHER INFORMATION: Xaa can be any naturally occurring amino acid

<400> SEQUENCE: 2

```
Met Ala Gln Pro Ala Met Ala Asp Tyr Lys Asp Val Val Met Thr Gln
1               5                   10                  15
Thr Pro Leu Thr Leu Ser Ile Thr Ile Gly Gln Pro Ala Ser Ile Ser
                20                  25                  30
Cys Lys Ser Ser Gln Ser Leu Leu Asp Ser Asp Gly Lys Thr Tyr Leu
            35                  40                  45
Asn Trp Leu Leu Gln Arg Pro Gly Gln Ser Pro Thr Arg Leu Ile Tyr
50                  55                  60
Leu Val Ser Lys Leu Asp Ser Gly Val Pro Asp Arg Phe Thr Gly Ser
65                  70                  75                  80
Gly Ser Gly Thr Asp Phe Thr Leu Lys Ile Ser Arg Val Glu Ala Glu
                85                  90                  95
Asp Leu Gly Ile Tyr Tyr Cys Trp Gln Gly Ala His Phe Pro Gln Thr
                100                 105                 110
Phe Gly Gly Gly Thr Lys Leu Glu Leu Lys Arg Gly Gly Gly Gly Ser
                115                 120                 125
Gly Gly Gly Gly Ser Gly Gly Gly Ser Gly Gly Gly Gly Ser Glu
            130                 135                 140
Val Gln Leu Gln Gln Thr Gly Pro Glu Leu Val Lys Pro Gly Ala Ser
145                 150                 155                 160
```

-continued

Val Lys Ile Ser Cys Lys Ala Ser Gly Tyr Ser Phe Thr Asp Tyr Ile
            165                 170                 175

Ile Phe Trp Val Lys Gln Ser His Gly Lys Ser Leu Glu Trp Thr Gly
            180                 185                 190

Asn Ile Asn Pro Tyr Tyr Gly Ser Thr Ser Tyr Asn Leu Lys Phe Lys
            195                 200                 205

Gly Lys Ala Thr Leu Thr Val Asp Lys Ser Ser Ser Thr Ala Tyr Met
210                 215                 220

Gln Leu Asn Ser Leu Thr Ser Xaa Asp Ser Ala Val Tyr Tyr Cys Val
225                 230                 235                 240

Arg Gly Val Tyr Tyr Gly Ser Ser Tyr Glu Ala Phe Pro Tyr Trp
            245                 250                 255

Gly Gln Gly Thr Leu Val Thr Val Ser Ala Ala Glu Leu Ala Ser
            260                 265                 270

Gly Gly Pro Glu Gly Gly Ser Leu Ala Ala Leu Thr Ala His Gln Ala
            275                 280                 285

Cys His Leu Pro Leu Glu Thr Phe Thr Arg His Arg Gln Pro Arg Gly
            290                 295                 300

Trp Glu Gln Leu Glu Gln Cys Gly Tyr Pro Val Gln Arg Leu Val Ala
305                 310                 315                 320

Leu Tyr Leu Ala Ala Arg Leu Ser Trp Asn Gln Val Asp Gln Val Ile
            325                 330                 335

Arg Asn Ala Leu Ala Ser Pro Gly Ser Gly Gly Asp Leu Gly Glu Ala
            340                 345                 350

Ile Arg Glu Gln Pro Glu Gln Ala Arg Leu Ala Leu Thr Leu Ala Ala
            355                 360                 365

Ala Glu Ser Glu Arg Phe Val Arg Gln Gly Thr Gly Asn Asp Glu Ala
370                 375                 380

Gly Ala Ala Asn Ala Asp Val Val Ser Leu Thr Cys Pro Val Ala Ala
385                 390                 395                 400

Gly Glu Cys Ala Gly Pro Ala Asp Ser Gly Asp Ala Leu Leu Glu Arg
            405                 410                 415

Asn Tyr Pro Thr Gly Ala Glu Phe Leu Gly Asp Gly Gly Asp Val Ser
            420                 425                 430

Phe Ser Thr Arg Gly Thr Gln Asn Trp Thr Val Glu Arg Leu Leu Gln
            435                 440                 445

Ala His Arg Gln Leu Glu Glu Arg Gly Tyr Val Phe Val Gly Tyr His
            450                 455                 460

Gly Thr Phe Leu Glu Ala Ala Gln Ser Ile Val Phe Gly Gly Val Arg
465                 470                 475                 480

Ala Arg Ser Gln Asp Leu Asp Ala Ile Trp Arg Gly Phe Tyr Ile Ala
            485                 490                 495

Gly Asp Pro Ala Leu Ala Tyr Ala Gln Asp Gln Glu Pro Asp
            500                 505                 510

Ala Arg Gly Arg Ile Arg Asn Gly Ala Leu Leu Arg Val Tyr Val Pro
            515                 520                 525

Arg Ser Ser Leu Pro Gly Phe Tyr Arg Thr Ser Leu Thr Leu Ala Ala
530                 535                 540

Pro Glu Ala Ala Gly Glu Val Glu Arg Leu Ile Gly His Pro Leu Pro
545                 550                 555                 560

Leu Arg Leu Asp Ala Ile Thr Gly Pro Glu Glu Gly Gly Arg Leu
            565                 570                 575

Glu Thr Ile Leu Gly Trp Pro Leu Ala Glu Arg Thr Val Val Ile Pro

-continued

```
                580                 585                 590
Ser Ala Ile Pro Thr Asp Pro Arg Asn Val Gly Gly Asp Leu Asp Pro
            595                 600                 605

Ser Ser Ile Pro Asp Lys Glu Gln Ala Ile Ser Ala Leu Pro Asp Tyr
        610                 615                 620

Ala Ser Gln Pro Gly Lys Pro Pro Arg Glu Asp Leu Lys
625                 630                 635

<210> SEQ ID NO 3
<211> LENGTH: 506
<212> TYPE: PRT
<213> ORGANISM: Artificial Sequence
<220> FEATURE:
<223> OTHER INFORMATION: EGbR201K (granzyme B mutant)-CD89(scFv)
<220> FEATURE:
<221> NAME/KEY: misc_feature
<222> LOCATION: (472)..(472)
<223> OTHER INFORMATION: Xaa can be any naturally occurring amino acid

<400> SEQUENCE: 3

Asp Asp Asp Asp Lys Ile Ile Gly Gly His Glu Ala Lys Pro His Ser
1               5                   10                  15

Arg Pro Tyr Met Ala Phe Leu Met Ile Trp Asp Gln Lys Ser Leu Lys
            20                  25                  30

Arg Cys Gly Gly Phe Leu Ile Arg Asp Asp Phe Val Leu Thr Ala Ala
        35                  40                  45

His Cys Trp Gly Ser Ser Ile Asn Val Thr Leu Gly Ala His Asn Ile
    50                  55                  60

Lys Glu Gln Glu Pro Thr Gln Gln Phe Ile Pro Val Lys Arg Ala Ile
65                  70                  75                  80

Pro His Pro Ala Tyr Asn Pro Lys Asn Phe Ser Asn Asp Ile Met Glu
                85                  90                  95

Thr Leu Gln Leu Glu Arg Lys Ala Lys Arg Thr Arg Ala Val Gln
            100                 105                 110

Pro Leu Arg Leu Pro Ser Asn Lys Ala Gln Val Lys Pro Gly Gln Thr
        115                 120                 125

Cys Ser Val Ala Gly Trp Gly Gln Thr Ala Pro Leu Gly Lys His Ser
    130                 135                 140

His Thr Leu Gln Glu Val Lys Met Thr Val Gln Glu Asp Arg Lys Cys
145                 150                 155                 160

Glu Ser Asp Leu Arg His Tyr Tyr Asp Ser Thr Ile Glu Leu Cys Val
                165                 170                 175

Gly Asp Pro Glu Ile Lys Lys Thr Ser Phe Lys Gly Asp Ser Gly Gly
            180                 185                 190

Pro Leu Val Cys Asn Lys Val Ala Gln Gly Ile Val Ser Tyr Gly Lys
        195                 200                 205

Asn Asn Gly Met Pro Pro Arg Ala Cys Thr Lys Val Ser Ser Phe Val
    210                 215                 220

His Trp Ile Lys Lys Thr Met Lys Arg Tyr Ala Glu His Glu Gly Asp
225                 230                 235                 240

Ala Ala Gln Pro Ala Met Ala Asp Tyr Lys Asp Val Val Met Thr Gln
                245                 250                 255

Thr Pro Leu Thr Leu Ser Ile Thr Ile Gly Gln Pro Ala Ser Ile Ser
            260                 265                 270

Cys Lys Ser Ser Gln Ser Leu Leu Asp Ser Asp Gly Lys Thr Tyr Leu
        275                 280                 285
```

```
Asn Trp Leu Leu Gln Arg Pro Gly Gln Ser Pro Thr Arg Leu Ile Tyr
    290                 295                 300

Leu Val Ser Lys Leu Asp Ser Gly Val Pro Asp Arg Phe Thr Gly Ser
305                 310                 315                 320

Gly Ser Gly Thr Asp Phe Thr Leu Lys Ile Ser Arg Val Glu Ala Glu
                325                 330                 335

Asp Leu Gly Ile Tyr Tyr Cys Trp Gln Gly Ala His Phe Pro Gln Thr
                340                 345                 350

Phe Gly Gly Gly Thr Lys Leu Glu Leu Lys Arg Gly Gly Gly Gly Ser
            355                 360                 365

Gly Gly Gly Gly Ser Gly Gly Gly Ser Gly Gly Gly Gly Ser Glu
    370                 375                 380

Val Gln Leu Gln Gln Thr Gly Pro Glu Leu Val Lys Pro Gly Ala Ser
385                 390                 395                 400

Val Lys Ile Ser Cys Lys Ala Ser Gly Tyr Ser Phe Thr Asp Tyr Ile
                405                 410                 415

Ile Phe Trp Val Lys Gln Ser His Gly Lys Ser Leu Glu Trp Thr Gly
            420                 425                 430

Asn Ile Asn Pro Tyr Tyr Gly Ser Thr Ser Tyr Asn Leu Lys Phe Lys
            435                 440                 445

Gly Lys Ala Thr Leu Thr Val Asp Lys Ser Ser Ser Thr Ala Tyr Met
    450                 455                 460

Gln Leu Asn Ser Leu Thr Ser Xaa Asp Ser Ala Val Tyr Tyr Cys Val
465                 470                 475                 480

Arg Gly Val Tyr Tyr Gly Ser Ser Tyr Glu Ala Phe Pro Tyr Trp
                485                 490                 495

Gly Gln Gly Thr Leu Val Thr Val Ser Ala
            500                 505

<210> SEQ ID NO 4
<211> LENGTH: 382
<212> TYPE: PRT
<213> ORGANISM: Artificial Sequence
<220> FEATURE:
<223> OTHER INFORMATION: CD89(scFv)-Ang GGRR (angiogenin mutant)
<220> FEATURE:
<221> NAME/KEY: misc_feature
<222> LOCATION: (219)..(219)
<223> OTHER INFORMATION: Xaa can be any naturally occurring amino acid

<400> SEQUENCE: 4

Met Thr Gln Thr Pro Leu Thr Leu Ser Ile Thr Ile Gly Gln Pro Ala
1               5                   10                  15

Ser Ile Ser Cys Lys Ser Ser Gln Ser Leu Leu Asp Ser Asp Gly Lys
                20                  25                  30

Thr Tyr Leu Asn Trp Leu Leu Gln Arg Pro Gly Gln Ser Pro Thr Arg
            35                  40                  45

Leu Ile Tyr Leu Val Ser Lys Leu Asp Ser Gly Val Pro Asp Arg Phe
50                  55                  60

Thr Gly Ser Gly Ser Gly Thr Asp Phe Thr Leu Lys Ile Ser Arg Val
65                  70                  75                  80

Glu Ala Glu Asp Leu Gly Ile Tyr Tyr Cys Trp Gln Gly Ala His Phe
                85                  90                  95

Pro Gln Thr Phe Gly Gly Gly Thr Lys Leu Glu Leu Lys Arg Gly Gly
            100                 105                 110

Gly Gly Ser Gly Gly Gly Gly Ser Gly Gly Gly Ser Gly Gly Gly
            115                 120                 125
```

```
Gly Ser Glu Val Gln Leu Gln Gln Thr Gly Pro Glu Leu Val Lys Pro
            130                 135                 140

Gly Ala Ser Val Lys Ile Ser Cys Lys Ala Ser Gly Tyr Ser Phe Thr
145                 150                 155                 160

Asp Tyr Ile Ile Phe Trp Val Lys Gln Ser His Gly Lys Ser Leu Glu
            165                 170                 175

Trp Thr Gly Asn Ile Asn Pro Tyr Tyr Gly Ser Thr Ser Tyr Asn Leu
            180                 185                 190

Lys Phe Lys Gly Lys Ala Thr Leu Thr Val Asp Lys Ser Ser Ser Thr
        195                 200                 205

Ala Tyr Met Gln Leu Asn Ser Leu Thr Ser Xaa Asp Ser Ala Val Tyr
    210                 215                 220

Tyr Cys Val Arg Gly Val Tyr Tyr Gly Ser Ser Tyr Glu Ala Phe
225                 230                 235                 240

Pro Tyr Trp Gly Gln Gly Thr Leu Val Thr Val Ser Ala Ala Ala Leu
            245                 250                 255

Glu Ser Arg Gln Asp Asn Ser Arg Tyr Thr His Phe Leu Thr Gln His
            260                 265                 270

Tyr Asp Ala Lys Pro Gln Gly Arg Asp Asp Arg Tyr Cys Glu Ser Ile
        275                 280                 285

Met Arg Arg Arg Gly Leu Thr Ser Pro Cys Lys Asp Ile Asn Thr Phe
    290                 295                 300

Ile His Gly Asn Lys Arg Ser Ile Lys Ala Ile Cys Glu Asn Lys Asn
305                 310                 315                 320

Gly Asn Pro His Arg Glu Asn Leu Arg Ile Ser Lys Ser Ser Phe Gln
            325                 330                 335

Val Thr Thr Cys Lys Leu His Arg Arg Ser Pro Trp Pro Pro Cys Gln
            340                 345                 350

Tyr Arg Ala Thr Ala Gly Phe Arg Asn Val Val Val Ala Cys Glu Asn
        355                 360                 365

Gly Leu Pro Val His Leu Asp Gln Ser Ile Phe Arg Arg Pro
            370                 375                 380
```

<210> SEQ ID NO 5
<211> LENGTH: 647
<212> TYPE: PRT
<213> ORGANISM: Artificial Sequence
<220> FEATURE:
<223> OTHER INFORMATION: CD89(scFv)-MAPtau
<220> FEATURE:
<221> NAME/KEY: misc_feature
<222> LOCATION: (222)..(222)
<223> OTHER INFORMATION: Xaa can be any naturally occurring amino acid

<400> SEQUENCE: 5

```
Asp Val Val Met Thr Gln Thr Pro Leu Thr Leu Ser Ile Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Thr Arg Leu Ile Tyr Leu Val Ser Lys Leu Asp Ser Gly Val Pro
50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Ile Tyr Tyr Cys Trp Gln Gly
```

```
                     85                  90                  95
Ala His Phe Pro Gln Thr Phe Gly Gly Gly Thr Lys Leu Glu Leu Lys
                100                 105                 110

Arg Gly Gly Gly Gly Ser Gly Gly Gly Ser Gly Gly Gly Gly Ser
            115                 120                 125

Gly Gly Gly Gly Ser Glu Val Gln Leu Gln Gln Thr Gly Pro Glu Leu
        130                 135                 140

Val Lys Pro Gly Ala Ser Val Lys Ile Ser Cys Lys Ala Ser Gly Tyr
145                 150                 155                 160

Ser Phe Thr Asp Tyr Ile Ile Phe Trp Val Lys Gln Ser His Gly Lys
                165                 170                 175

Ser Leu Glu Trp Thr Gly Asn Ile Asn Pro Tyr Tyr Gly Ser Thr Ser
            180                 185                 190

Tyr Asn Leu Lys Phe Lys Gly Lys Ala Thr Leu Thr Val Asp Lys Ser
        195                 200                 205

Ser Ser Thr Ala Tyr Met Gln Leu Asn Ser Leu Thr Ser Xaa Asp Ser
    210                 215                 220

Ala Val Tyr Tyr Cys Val Arg Gly Val Tyr Tyr Gly Ser Ser Tyr
225                 230                 235                 240

Glu Ala Phe Pro Tyr Trp Gly Gln Gly Thr Leu Val Thr Val Ser Ala
                245                 250                 255

Ala Ala Met Ala Glu Pro Arg Gln Glu Phe Glu Val Met Glu Asp His
            260                 265                 270

Ala Gly Thr Tyr Gly Leu Gly Asp Arg Lys Asp Gln Gly Gly Tyr Thr
        275                 280                 285

Met His Gln Asp Gln Glu Gly Asp Thr Asp Ala Gly Leu Lys Ala Glu
    290                 295                 300

Ala Gly Ile Gly Asp Thr Pro Ser Leu Glu Asp Glu Ala Ala Gly His
305                 310                 315                 320

Val Thr Gln Ala Arg Met Val Ser Lys Ser Lys Asp Gly Thr Gly Ser
                325                 330                 335

Asp Asp Lys Lys Ala Lys Gly Ala Asp Gly Lys Thr Lys Ile Ala Thr
            340                 345                 350

Pro Arg Gly Ala Ala Pro Pro Gly Gln Lys Gly Gln Ala Asn Ala Thr
        355                 360                 365

Arg Ile Pro Ala Lys Thr Pro Ala Pro Lys Thr Pro Ser Ser
    370                 375                 380

Gly Glu Pro Pro Lys Ser Gly Asp Arg Ser Gly Tyr Ser Ser Pro Gly
385                 390                 395                 400

Ser Pro Gly Thr Pro Gly Ser Arg Ser Arg Thr Pro Ala Leu Pro Thr
                405                 410                 415

Pro Pro Thr Arg Glu Pro Lys Lys Val Ala Val Val Arg Thr Pro Pro
            420                 425                 430

Lys Ser Pro Ser Ser Ala Lys Ser Arg Leu Gln Thr Ala Pro Val Pro
        435                 440                 445

Met Pro Asp Leu Lys Asn Val Lys Ser Lys Ile Gly Ala Thr Glu Asn
    450                 455                 460

Leu Lys His Gln Pro Gly Gly Gly Lys Val Gln Ile Ile Asn Lys Lys
465                 470                 475                 480

Leu Asp Leu Ser Asn Val Gln Ser Lys Cys Gly Ser Lys Asp Asn Ile
                485                 490                 495

Lys His Val Pro Gly Gly Gly Ser Val Gln Ile Val Tyr Lys Pro Val
            500                 505                 510
```

```
Asp Leu Ser Lys Val Thr Ser Lys Cys Gly Ser Leu Gly Asn Ile His
            515                 520                 525

His Lys Pro Gly Gly Gly Gln Val Glu Val Lys Ser Glu Lys Leu Asp
        530                 535                 540

Phe Lys Asp Arg Val Gln Ser Lys Ile Gly Ser Leu Asp Asn Ile Thr
545                 550                 555                 560

His Val Pro Gly Gly Gly Asn Lys Lys Ile Glu Thr His Lys Leu Thr
                565                 570                 575

Phe Arg Glu Asn Ala Lys Ala Lys Thr Asp His Gly Ala Glu Ile Val
            580                 585                 590

Tyr Lys Ser Pro Val Val Ser Gly Asp Thr Ser Pro Arg His Leu Ser
        595                 600                 605

Asn Val Ser Ser Thr Gly Ser Ile Asp Met Val Asp Ser Pro Gln Leu
    610                 615                 620

Ala Thr Leu Ala Asp Glu Val Ser Ala Ser Leu Ala Lys Gln Gly Leu
625                 630                 635                 640

Pro Lys Lys Lys Arg Lys Val
                645

<210> SEQ ID NO 6
<211> LENGTH: 206
<212> TYPE: PRT
<213> ORGANISM: Homo sapiens

<400> SEQUENCE: 6

Gln Glu Gly Asp Phe Pro Met Pro Phe Ile Ser Ala Lys Ser Ser Pro
1               5                   10                  15

Val Ile Pro Leu Asp Gly Ser Val Lys Ile Gln Cys Gln Ala Ile Arg
            20                  25                  30

Glu Ala Tyr Leu Thr Gln Leu Met Ile Ile Lys Asn Ser Thr Tyr Arg
        35                  40                  45

Glu Ile Gly Arg Arg Leu Lys Phe Trp Asn Glu Thr Asp Pro Glu Phe
    50                  55                  60

Val Ile Asp His Met Asp Ala Asn Lys Ala Gly Arg Tyr Gln Cys Gln
65                  70                  75                  80

Tyr Arg Ile Gly His Tyr Arg Phe Arg Tyr Ser Asp Thr Leu Glu Leu
                85                  90                  95

Val Val Thr Gly Leu Tyr Gly Lys Pro Phe Leu Ser Ala Asp Arg Gly
            100                 105                 110

Leu Val Leu Met Pro Gly Glu Asn Ile Ser Leu Thr Cys Ser Ser Ala
        115                 120                 125

His Ile Pro Phe Asp Arg Phe Ser Leu Ala Lys Glu Gly Glu Leu Ser
    130                 135                 140

Leu Pro Gln His Gln Ser Gly Glu His Pro Ala Asn Phe Ser Leu Gly
145                 150                 155                 160

Pro Val Asp Leu Asn Val Ser Gly Ile Tyr Arg Cys Tyr Gly Trp Tyr
                165                 170                 175

Asn Arg Ser Pro Tyr Leu Trp Ser Phe Pro Ser Asn Ala Leu Glu Leu
            180                 185                 190

Val Val Thr Asp Ser Ile His Gln Asp Tyr Thr Thr Gln Asn
        195                 200                 205
```

ANTI-CD89 CYTOTOXIC COMPLEX

CROSS REFERENCE TO RELATED APPLICATIONS

This is a US national phase application under 35 USC § 371 of international patent application no. PCT/EP2015/056386, filed Mar. 25, 2015, herein incorporated by reference in its entirety.

REFERENCE TO SEQUENCE LISTING SUBMITTED ELECTRONICALLY

The official copy of the sequence listing is submitted electronically via EFS-Web as an ASCII formatted sequence listing with file "PCTEP2015056386_SEQ_ID" created on 9 Sep. 2017, filed on 22 Sep. 2017 and having a size of 24 Kilobytes. The sequence listing contained in this ASCII formatted document forms part of the specification and is herein incorporated by reference in its entirety.

FIELD OF THE INVENTION

The technology provided herein relates to novel complexes suitable for targeting and killing a human target cell comprising a first polypeptide with a binding structure for binding the complex to the cellular surface receptor CD89 presented on the cell surface of the human target cell and a second polypeptide comprising a toxic effector domain; to nucleic acid molecules encoding said complexes, vectors, host cells containing the nucleic acids and methods for preparation and producing such complexes; compositions and methods for using said complexes for the treatment of diseases, in particular of cancer diseases like leukemia.

BACKGROUND OF THE INVENTION

In the treatment of tumors, autoimmune diseases, allergies and tissue rejection reactions, it is a disadvantage that the currently available medicaments, such as chemotherapeutic agents (Goodin, S., Am J Health Syst Pharm, 2007, 64: p. 15-24) corticosteroids (Stanbury, R. M. & Graham, E. M., Br J Ophthalmol, 1998, 82: p. 704-708) and immunosuppressive agents (Stucker, F. & Ackermann, D., Ther Umsch, 2011, 68: p. 679-686), have a potential of side effects which is sometimes considerable, due to their relative non-specificity. It has been attempted to moderate this by various therapeutical concepts. Especially the use of immunotherapeutic agents is an approach, which resulted in an increase of the specificity of medicaments, especially in tumor treatment.

Immunotoxins (ITs) are proteins originally developed for the treatment of malignant diseases. They comprise a toxic effector domain and a tumor cell-specific binding component, which is usually an antibody or a derivative thereof. Initially the antibody components were derived from mice and the toxins were derived from bacteria or plants, e.g. *Pseudomonas aeruginosa* exotoxin A (ETA) (Ribbert, T., et al., Br J Dermatol, 2010; 163: p. 279-86), diphtheria toxin (DT) (Potala, S., et al., Drug discovery today, 2008, 13: p. 807-15) or ricin A toxin (RT) (Thepen T., et al., Nature biotechnology, 2000, 18: p. 48-51.). The major advantage of ITs compared to traditional chemotherapy is their exceptional specificity towards targeted cells.

Fusion proteins that consist of a disease-specific binding component (e.g. scFvs, cytokines or peptide ligands) fused to a human toxic effector domain like a pro-apoptotic enzyme are known as 'human cytolytic fusion proteins' (hCFPs) and have already proven their potential in several applications (Stahnke, B., et al., Mol Cancer Ther, 2008. 7(9): p. 2924-32; Huhn, M., et al., Cancer Res, 2001. 61(24): p. 8737-42; Krauss, J., et al., Br J Haematol, 2005. 128(5): p. 602-9; Schiffer, S., et al., Antibodies, 2013. 2(1): p. 9-18; Hristodorov, D., et al., Br J Cancer, 2014. 109(6): p. 1570-1578).

The therapeutic activity of most anticancer drugs in clinical use is limited by their general toxicity to proliferating cells, including some normal cells. Although, chemists continue to develop novel cytotoxic agents with unique mechanisms of action, many of these compounds still lack tumor selectivity and have not been therapeutically useful. Antibodies or fragments ablated thereof meaning also ITs and hCFPs bind to specific markers on the surface of cancer cells offer an alternative therapy that is tumor highly specific and thus much less toxic (Chari, R V, Accounts of chemical research, 2008, 41: p. 98-107).

However, in order to obtain the desired cytotoxic effect of ITs and/or hCFPs some processing steps in the targeted cells are crucial. Next to the necessary binding and internalization of the IT- or hCFP-antigen complex, key impact on the activity has the subsequent intracellular routing with and cytosolic delivery Berges, N., et al. Antibodies, 2014, 3(1): p. 92-115).

An example is the treatment of leukaemia using immunotherapy, which requires the targeting of specific antigens on the surface of blasts. The Fc gamma receptor (FcγRI, CD64) has been investigated into details. The CD64-targeting immunotherapy has shown promising efficacy in the targeted ablation of acute myeloid leukaemia (AML) and chronic myeloid leukaemia (CML) cells. Thus far, CD64 is the only Fc receptor deemed suitable as an immunotherapeutic target for both oncogenic and inflammatory diseases. Nevertheless, there are plenty of clinical cases of malignancies lacking the CD64 expression (Schiffer, S., et al., Int J Cancer, 2014, 135: p. 1497-508), which excludes the possibility of efficient CD64-targeting therapy.

Furthermore, the cytotoxic efficacy of the IT- or hCFP is crucially dependent on the used scFv and the subsequent intracellular routing occurring after the IT- or hCFP-antigen complex internalization. Thus, the chosen scFv, in combination with the toxic effector domain, has to fulfill several requirements in order to acquire IT- or CFP cytotoxicity.

As a result thereof, the availability of novel ITs or human cytolytic fusion proteins comprising new binding moiety, which covers all requirements, would be highly advantageous.

SUMMARY OF THE INVENTION

In a first aspect, the present disclosure pertains to selected and specific complexes suitable for targeting and killing a human target cell, in particular a human cancer cell, comprising a first polypeptide having a binding structure for binding the complex to the cellular surface receptor CD89 presented on the cell surface of said human target cell and a second polypeptide comprising a toxic effector domain.

Therefore, embodiments of the disclosure provides cytotoxic recombinant ITs and human cytolytic fusion proteins (hCFPs), for example which are suitable to induce apoptosis in human cells, comprising a target cell-specific binding component and a toxic effector domain, wherein the binding component comprises an antibody or an antibody fragment with an antigen-binding site for binding to the cellular surface receptor CD89.

In still another aspect, embodiments of this disclosure provide nucleic acids encoding complexes, in particular recombinant fusion proteins as disclosed herein, as well as vectors and host cells comprising such nucleic acids.

In other aspects, the present disclosure relates to compositions comprising the complexes according to the present disclosure, in particular the recombinant fusion proteins as described herein, wherein the complexes may be useful for, or used in therapeutical, cosmetic and/or diagnostic applications. In an advantageous embodiment, the compositions are used as a therapeutical composition for the treatment of cancer, in particular in the treatment of leukemia.

In still another aspect, embodiments of this disclosure provide medicaments or pharmaceutical composition comprising a complex according to the present disclosure in combinations with a pharmacologically acceptable carrier, diluent, stabilizer or formulation.

In a further aspect, embodiments of the present disclosure relate to methods for producing the complexes, in particular for producing the recombinant fusion proteins in a host cell by transforming the host cell with a DNA construct, advantageously including a promoter having transcriptional activity in the host cell, cultivating the transformed host cell in a suitable culture medium to allow expression of said fusion proteins and producing said fusion proteins. The method may also include isolating/purifying the produced fusion proteins.

A further aspect pertains to methods of treating a malignant disease, an allergy, an autoimmune reaction, a tissue rejection reaction, or a chronic inflammation reaction comprising administering an effective amount of a complex or a pharmaceutical composition according to the present disclosure to a patient in need thereof.

A further aspect relates to polypeptides suitable for the detection of CD89, wherein said polypeptide comprises the amino acid sequence of SEQ ID NO: 1, or a homologous polypeptide, variant or mutation thereof having an amino acid which is at least 85%, preferably 90%, more preferably 95% identical to the amino acid sequence of SEQ ID NO. 1, which are produced by recombinant or synthetic methods by substitution, insertion, addition or deletion of one or more amino acid residues, or fragments thereof.

Another aspect of the present disclosure pertains to methods for the detection of CD89 contained in a sample, comprising:

(a) contacting a sample with a polypeptide with a fusion tag specific fluorophore that specifically bind the fusion tag coupled to said polypeptide; and (b) detecting the presence of CD89 in the sample by fluorescence signals associated with the fusion tag specific fluorophore.

Therefore, aspects of the present disclosure pertains also to methods for the diagnosis of CD89+ malignancies, comprising administering to a patient a polypeptide suitable for the detection of CD89 as described herein or contacting a biological sample taken from a patient with a polypeptide suitable for the detection of CD89 as described herein.

Before the disclosure is described in detail, it is to be understood that this disclosure is not limited to the particular complexes, in particular the ITs and hCFPs and production methods described in the present disclosure. It is also to be understood that the terminology used herein is for purposes of describing particular embodiments only, and is not intended to be limiting. It must be noted that, as used in the specification and the appended claims, the singular forms "a," "an" and "the" include singular and/or plural referents unless the context clearly dictates otherwise. It is moreover to be understood that, in case parameter ranges are given which are delimited by numeric values, the ranges are deemed to include these limitation values.

BRIEF DESCRIPTION OF THE DRAWINGS

FIGS. 3 (B) and (C) show the design of the GbR201K-CD89(scFv) vector and CD89(scFv)-Ang GGRR or MAPtau vector, respectively. Igκ leader, leader sequence for the secretion of the protein into the cell culture supernatant; EGbR201K, a mutant form of human derived granzyme B; Ang GGRR, a mutant form of human derived angiogenin; MAPtau, the human derived microtubule associated protein Tau.

FIGS. 4 (B), (C) and (D) show CD89(scFv)-Ang GGRR [47 kDa], CD89 (scFv)-MAPtau [80 kDa] and EGbR201K-CD89(scFv) [59 kDa], respectively, analyzed on SDS-polyacrylamide gel stained with Coomassie Brilliant Blue (Coo) and corresponding Western blot (WB) probed with a mouse anti-poly histidin primary mAb and an AP-conjugated goat anti-mouse secondary mAb.

FIG. 5 (B) is showing the specific binding of the CD89(scFv)-fusion proteins to TNFα-stimulated CD89+ HL-60 and CD89– Ramos cells analyzed by flow cytometry with a Alexa488 coupled mouse anti-polyhistidine mAb.

FIG. 6 (B) shows an RNase in vitro cleavage assay. An yeast tRNA was incubated with several concentrations of the CD89(scFv)-Ang GGRR at 37° C. for 1.5 hour (100 ng RNase A was used as a positive control and RNase-free water was added to the negative control sample). To visualize the dose-dependent degradation process, the samples were separated by 1% RNase-free agarose gel electrophoresis and fragment bands were detected under UV light.

FIG. 7 (B) indicates the quantitative analysis of dot blots at increasing CD89(scFv)-ETA' concentrations. Cell death is shown as the sum of early and late apoptotic/necrotic cells measured by AnnexinV/PI staining. FIG. 7 (C) shows the apoptotic effect of 300 nM CD89(scFv)-Ang GGRR and 300 nM GbR201K-CD89 (scFv) on HL60 cells (CD89$^+$) and Ramos cells (CD89$^-$) both stimulated with 3000/ml IFNγ is measured using AnnexinV/PI staining. Data represent mean values with standard deviations of triplicates. Statistical significance was determined via two-tailed unpaired Student's t-test, (*): $p<0.05$, : $p<0.01$, (*): $p<0.001$.

FIG. 11 and FIG. 12 show sequence embodiments of the present disclosure.

DETAILED DESCRIPTION OF THE INVENTION

Figure 1:
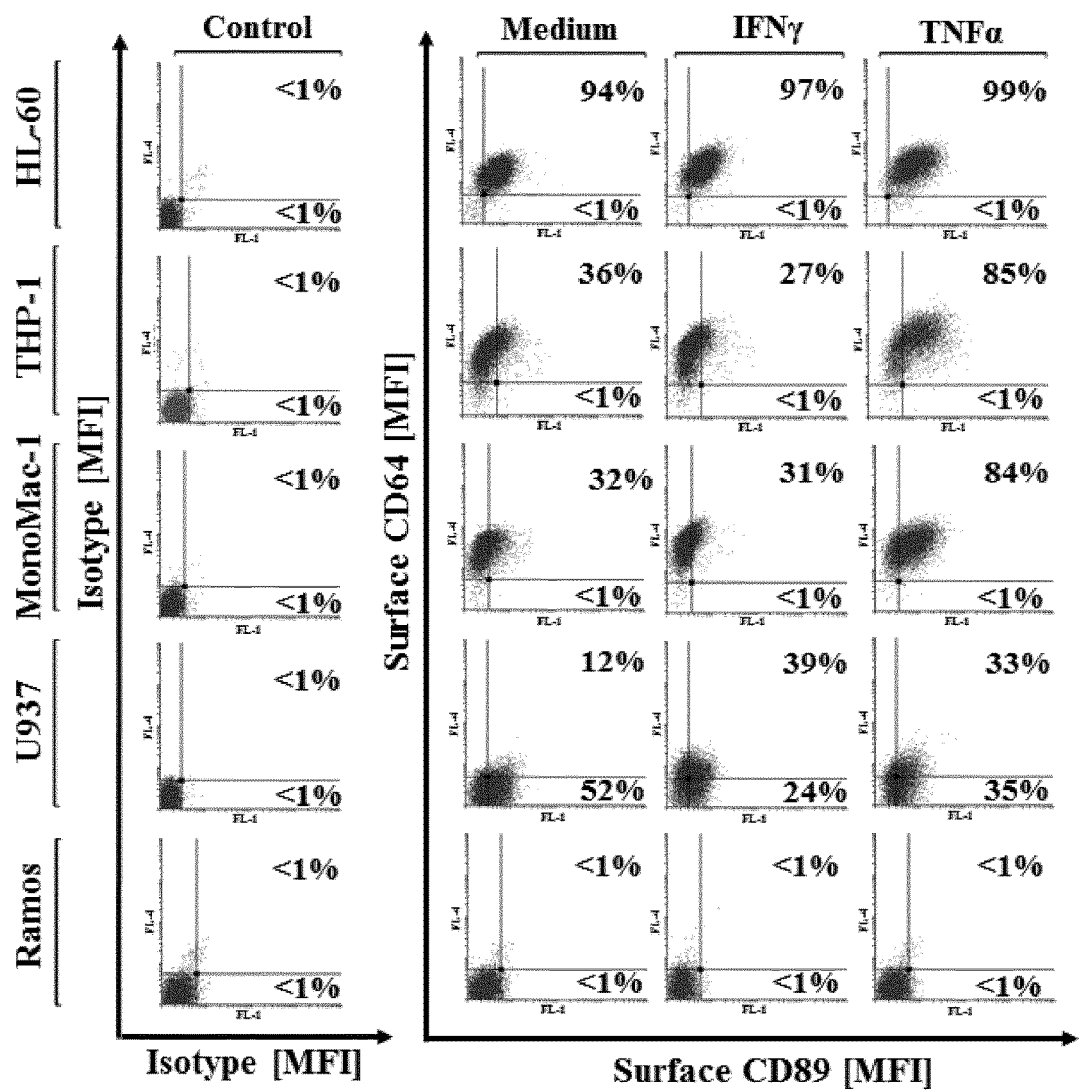
FIG. 1 is a diagram showing CD89 and CD64 expression profiles of human AML and U937 histiocytic lymphoma cells. Human AML cells (HL-60, THP-1 and Mono-Mac-1), histiocytic lymphoma cells (U937), and Burkitt lymphoma cells (Ramos) were incubated with medium only or stimulated with either 100 U/ml IFNγ or 1000 U/ml TNFα for 24 h prior to measurement. Double staining for CD64 and CD89 was carried out and dot blotted against an isotype control. All detection antibodies were prepared in PBS with 1% (v/v) blocking human serum. Red: gated population of viable cells.

The present disclosure provides potent, novel immunotherapeutic agents, in particular complexes suitable for CD89-specific targeting and killing/destroying of human cancer cells.

According to the present disclosure, the therapeutic potential of FcαRI (CD89) as a new target polypeptide immunotoxin target antigen expressed by different cancer cells like myeloid leukemic cell populations for immunotoxins (ITs) or human cytolytic fusion proteins (hCFPs) is shown the first time with the present disclosure. Some embodiment of the present disclosure pertains to isolated a recombinant fusion proteins comprising an anti-human CD89 single chain fragment variable (scFv) and the well-characterized truncated version of the potent *Pseudomonas* exotoxin A (ETA').

These novel therapeutic approach achieved in vitro $EC_{50}$ values in range 0.2-3 nM depending on applied stimuli, i.e. interferon gamma (IFNγ) or tumour necrosis factor α (TNFα).

A dose-dependent apoptosis-mediated cytotoxicity was also observed, which resulted in the eradication of up to 90% of the target cells within 72 h. These findings were also confirmed ex vivo using e.g. leukaemic primary cells from peripheral blood samples.

CD89-specific targeting of leukaemia cell lines can be achieved in vitro and the efficient elimination of leukaemic primary cells supports the potential of CD89-ETA' as a potent, novel immunotherapeutic agent.

Therefore, in a first aspect the present disclosure pertains to selected and specific complexes suitable for targeting and killing human target cells, in particular of human cancer cells, comprising a first polypeptide with a binding structure for binding said complex to the cellular surface receptor CD89 presented on the cell surface of said human target cell and a second polypeptide comprising a toxic effector domain.

Advantageous embodiments of the present disclosure pertains to Immunotoxins (ITs) and recombinant human cytolytic fusion proteins (hCFPs) suitable for killing a target cell like a human cancer cell, e.g. by inducing apoptosis, comprising a target cell-specific binding component (binding structure) and a toxic effector domain, wherein the binding component comprises an antibody or an antibody fragment with an antigen-binding site for binding to the cellular surface receptor CD89 presented on the surface of the target cell.

In an advantageous embodiment, the complex or at least the toxic effector domain are transferred into the target cell. Therefore, the toxic effector domain is preferably transferable into the target cell after binding to the CD89 protein.

The terms "polypeptide", "peptide", or "protein" are used interchangeably herein to designate a linear series of amino acid residues connected one to the other by peptide bonds between the alpha-amino and carboxyl groups of adjacent residues. The amino acid residues are preferably in the natural "L" isomeric form. However, residues in the "D"

isomeric form can be substituted for any L-amino acid residue, as long as the desired functional property is retained by the polypeptide. In addition, the amino acids, in addition to the 20 "standard" amino acids, include modified and unusual amino acids.

As mentioned above, the present disclosure relates to isolated/purified complexes, in particular isolated recombinant fusion proteins, comprising at least one component A (binding structure) and at least one component B (toxic effector domain), characterized in that component A has a binding activity for the cellular surface receptor CD89 presented on the surface of a target cell, and component B is a compound having cytotoxic and/or cytolytic activity.

The terms "recombinant fusion protein" and "fusion protein" are used herein interchangeably to refer for example to a protein produced by recombinant technology which comprises segments i.e. amino acid sequences, from heterologous sources, such as different proteins or different organisms. The segments are joined either directly or indirectly to each other via peptide bonds. By indirect joining it is meant that an intervening amino acid sequence, such as a peptide linker is juxtaposed between segments forming the fusion protein. A recombinant fusion protein is encoded by a nucleotide sequence, which is obtained by genetically joining nucleotide sequences derived from different regions of one gene and/or by joining nucleotide sequences derived from two or more separate genes.

Furthermore, the encoding nucleotide sequences may be synthesized in vitro without the need for initial template DNA samples e.g. by oligonucleotide synthesis from digital genetic sequences and subsequent annealing of the resultant fragments. Desired protein sequences can be "reverse translated" e.g. using appropriate software tools. Due to the degeneracy of the universal genetic code, synonymous codons within the open-reading frame (i.e. the recombinant protein coding region) can be exchanged in different ways, e.g. to remove cis-acting instability elements (e.g. AUUUA), to remove, introduce or modify the secondary and tertiary mRNA structures (e.g. pseudoknots, stem-loops, . . . ), to avoid self-complementary regions that might trigger post-transcriptional gene silencing (PGTS), to change the overall AT:GC content, or to adjust the codon-usage to the expression host. Such changes can be designed manually or by using appropriate software tools or through a combination.

A complex comprising a first polypeptide having binding activity for the cellular surface receptor CD89 presented on the surface of a CD89 expressing target cell and a second polypeptide comprising a toxic effector domain can be a recombinant product prepared using recombinant DNA methodology and expression in a suitable host cell, as is known in the art (see for example (Sambrook, J. & Russell, D., Molecular Cloning: a Laboratory Manual, 2001, 3rd ed).

In an advantageous embodiment, the complexes according to the present disclosure, in particular the recombinant fusion proteins are isolated. The term "isolated" when used in relation to a nucleic acid or protein refers to a nucleic acid sequence or protein that is identified and separated from at least one contaminant (nucleic acid or protein, respectively) with which it is ordinarily associated in its natural source. Isolated nucleic acid or protein is present in a form or setting that is different from that in which it is found in nature. In contrast, non-isolated nucleic acids or proteins are found in the state they exist in nature.

According to the present disclosure, the first polypeptide comprising a binding structure (component A) and the second polypeptide comprising a toxic effector domain (component B) are preferably linked to each other in a complex. "Linked" refers to non-covalent or covalent bonding between two or more molecules. Linking may be direct or indirect. Two molecules are indirectly linked when the two molecules are linked via a connecting molecule (linker). Two molecules are directly linked when there is no intervening molecule linking them. As mentioned above, the isolated protein domains are linked either directly or indirectly to each other, preferably via peptide bonds or disulfide bonds. An example of indirect covalent linking is that an intervening amino acid sequence, such as a peptide linker is juxtaposed between segments forming the fusion protein.

In some embodiments, the components A and B are directly linked to each other. In other embodiments, the components are indirectly linked to each other via a linker, wherein in some examples the linker is a polypeptide with a size of less or equal twenty amino acids, in particular 2 to 6 amino acids.

The term "binding structure" used herein comprises polypeptides having a binding activity for the cellular surface receptor CD89, in particular to the extracellular part of CD89 (SEQ ID NO. 6). For example, the polypeptide comprises a cell targeting moiety that is a moiety that binds to and/or is internalized by only a selected population of cells such as cells expressing the cellular receptor CD89. Such a cell targeting moiety may, for example, comprise an antibody, a growth factor, a hormone, a cytokine, an aptamer or an avimer that binds to CD89. Examples for binding moieties comprised in the ligand are affinity moieties from affinity substances or affinity substances in their entirety selected from the group consisting of antibodies, antibody fragments, receptor ligands, enzyme substrates, lectins, cytokines, lymphokines, interleukins, angiogenic or virulence factors, allergens, peptidic allergens, recombinant allergens, allergen-idiotypical antibodies, autoimmune-provoking structures, tissue-rejection-inducing structures, immunoglobulin constant regions and their derivatives, mutants or combinations thereof. In particular the target cell-specific binding component specifically binds to CD89.

In an advantageous embodiment, the binding structure is an antibody or an antibody fragment selected from the group consisting of a monoclonal antibody, Fab, scFv; single domain, or a fragment thereof, bis scFv, $Fab_2$, $Fab_3$, minibody, diabody, triplebody, tetrabody and tandab.

An antibody is in particular specific for a particular antigen if it binds that particular antigen in preference to other antigens. In particular, the antibody may not show any significant binding to molecules other than that particular antigen, and specificity may be defined by the difference in affinity between the target antigen and other non-target antigens. An antibody may also be specific for a particular epitope which may be carried by a number of antigens, in which case the antibody will be able to bind to the various antigens carrying that epitope. For example, specific binding may exist when the dissociation constant for a dimeric complex of antibody and antigen is 1 µM, preferably 100 nM and most preferably 1 nM or lower.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain (VL) and variable heavy chain (VH) refer to these light and heavy chains, respectively.

Antibodies exist as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to V.sub.H-C.sub.H1 by a disulfide bond. The F(ab)'2 may be reduced under mild conditions to break the disulfide linkage in the hinge region thereby converting the (Fab')2 dimer into two Fab' monomers. The Fab' monomer is essentially a Fab with part of the hinge region (Paul, W E., Fundamental immunology, 1993, 3rd ed). While various antibody fragments are defined in terms of the digestion of an intact antibody, one of skill will appreciate that such Fab' fragments may be synthesized de novo either chemically or by utilizing recombinant DNA technology. Thus, the term antibody, as used herein also includes antibody fragments either produced by the modification of whole antibodies or synthesized de novo using recombinant DNA technologies. Preferred antibodies include single chain antibodies (antibodies that exist as a single polypeptide chain), more preferably single chain Fv antibodies (scFv) in which a variable heavy and a variable light chain are joined together (directly or through a peptide linker) to form a continuous polypeptide. The single chain Fv antibody is a covalently linked VH-VL heterodimer which may be expressed from a nucleic acid including VH- and VL-encoding sequences either joined directly or joined by a peptide-encoding linker (Huston, J S., et al., Proc Natl Acad Sci USA, 1988, 85: p. 5879-83). While the VH and VL are connected to each as a single polypeptide chain, the VH and VL domains associate non-covalently.

An "antigen-binding site" or "binding moiety" in an antibody or antibody fragment refers to the part of an immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions" or "FRs". Thus, the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen binding "surface". This surface mediates recognition and binding of the target antigen. The three hypervariable regions of each of the heavy and light chains are referred to as "complementarity determining regions" or "CDRs" and are characterized, for example by Kabat et al. Sequences of proteins of immunological interest, 4th ed. U.S. Dept. Health and Human Services, Public Health Services, Bethesda, Md. (1987).

Therefore, the term antibody includes, but is not limited to, polyclonal antibodies, monoclonal antibodies, single chain antibodies, humanized antibodies, minibodies, diabodies, triplebodies as well as antibody fragments, such as Fab', Fab, F(ab')2, single domain antibodies. In an advantageous embodiment, the antibody is a human antibodies and the antibody fragment is a human antibody fragment.

Therefore, as mentioned above, the binding structure is preferably an antibody or an antibody fragment selected from the group consisting of a monoclonal antibody, Fab, scFv; single domain, or a fragment thereof, bis scFv, $Fab_2$, $Fab_3$, minibody, diabody, triplebody, tetrabody and tandab that is able to bind to the cellular surface receptor CD89 presented on the cell surface of said human target cell.

The binding activity of the targeting moiety can be verified by flow cytometry assisted measurement using said human target cells in appropriate stage and appropriate detection antibodies suitable for the mentioned analysis.

In an advantageous embodiment, the complex according to the present disclosure comprises a CD89-specific single-chain variable fragment (scFv) as the binding structure for binding the complex to the cellular surface receptor CD89 presented on the cell surface of a human target cell.

As used herein, the term "single chain antibody fragments" (scFv) refers to antibodies prepared by determining the binding domains (both heavy and light chains) of a binding antibody, and supplying a linking moiety, which permits preservation of the binding function. This forms, in essence, a radically abbreviated antibody, having only that part of the variable domain necessary for binding to the antigen. Determination and construction of single chain antibodies are described in U.S. Pat. No. 4,946,778 by Ladner et al.

In an advantageous embodiment, the binding structure is a human or humanized antibody or an antibody fragment. As used herein, the term "human antibody" or "human antibody fragment" means that the framework regions of an immunoglobulin or an immunoglobulin fragment are derived from human immunoglobulin sequences. In an advantageous embodiment, the binding structure is a human or humanized antibody or an antibody fragment.

The phrase "specifically binds to CD89" refers to a binding reaction, which is determinative of the presence of the CD89 protein in the presence of a heterogeneous population of proteins and other biologics. Thus, under designated immunoassay conditions, the specified antibodies or antibody fragments bind to CD89 and do not bind in a significant amount to other proteins present in the sample. Specific binding to a protein under such conditions may require an antibody or antibody fragment that is selected for its specificity for CD89.

The binding activity of the targeting moiety can be verified by flow cytometry assisted measurement using said human target cells in appropriate stage and appropriate detection antibodies suitable for the mentioned analysis.

As used herein, the term "CD89" refers to a human surface Fc alpha-receptor (FcαR, CD89). Under normal physiological conditions the Fc alpha-receptor is present on monocytes, neutrophils, macrophages and eosinophils. Its biological function is to interact with IgA-opsonised targets, triggering several immunological defence processes, e.g. phagocytosis, antibody-dependent cell-mediated cytotoxicity, and the stimulation of inflammatory mediators (Morton, H C. & Brandtzaeg, P., Arch Immunol Ther Exp 1 2001; 49: 217-29). In many human tissues, most of the CD89+ cells are neutrophils and monocytes/macrophages. Furthermore, although monocytes in the blood express relatively high levels of CD89, most tissue macrophages (particularly those located in the gut lamina propria) tend not to express CD89 on the surface, with a parallel down regulation of CD14 (Hamre, R., et al., Scand J Immunol, 2003, 57: p. 506-16).

This suggests that the abundance of CD89 depends on the differentiation stage of myeloid cells. The biological relevance of CD89 down regulation during the maturation of myeloid precursor cells is unknown.

On the other hand, the presence of anomalous numbers of myeloid cells in the blood is indicative of several myelogenous haematological malignancies, with AML and CML the most common (Horner, M J R L., et al., National Cancer Institute, 2009). The different forms of myeloid leukaemia have been categorised using the French-American-British (FAB) system into eight subtypes (M0-M7) and the World Health Organisation (WHO) uses similar criteria (Sander, C A., et al., Clin Lymphoma 2001, 2: p 86-100). A standard panel of markers is used for detailed diagnosis and classification, including FcγRI (CD64) that is present on AML subtypes M0-M5 in varying degrees (Dunphy, C H. and Tang W., Archives of pathology & laboratory medicine, 2007, 131: p. 748-54). Thus far, there was no evidence that other Fc receptors can be used as diagnostic antigens or therapeutic targets in AML or other forms of myeloid leukaemia.

As used herein, the expression "killing a human target cell" is to be understood as implying an inhibition of protein synthesis or induction of apoptosis resulting in elimination or death of these cells; various molecular mechanisms may be employed; for example mechanisms that alter the function of a cell, those that alter the gene expression pattern of a cell or those that directly affect the viability of a cell may be used.

As used "killing a human target cell" herein may also comprise to inhibit the cell growth (e.g., referring to cells) intending to include any measurable decrease in the growth of a cell when contacted with an anti-CD89 complex according to the present disclosure as compared to the growth of the same cell not in contact with an anti-CD89 complex according to the present disclosure, e.g., the inhibition of growth of a cell by at least about 10%, 20%, 30%, 40%, 50%, 60%, 70%, 80%, 90%, 99%, or 100%.

As used herein, the expression "CD89 expressing cells" refers to cells with CD89 as surface antigen. Any type of cell expressing CD89 may be envisaged for treatment with the cytotoxic/cytolytic complexes of the present disclosure.

A "target cell" refers to a cell or cell-type characterized by the expression or overexpression of the target molecule CD89 that is for example characteristic for some tumor cells like leukemia cells including myeloid leukaemic cells. CD89 (FcαR) was initially identified on the surface of several human phagocytic cells, including neutrophils, monocytes and macrophages. CD89-expressing immune cells have a protective function in the immune system, but they are also involved in pathogenesis of different diseases. For example, neutrophils contribute to several autoimmune disorders (e.g. systemic lupus erythematosus), inflammatory disorders, NETosis and cystic fibrosis.

"Target cell" shall mean further any undesirable cell in a subject (e.g., a human or animal) that can be targeted by a complex or polypeptide of the present disclosure. In one embodiment, the target cell is a cell expressing or overexpressing CD89. In another embodiment, target cells include tumor cells. Tumor cells that can be targeted are tumor cells of any type of cancer, including cancer of breast, ovarian, prostate, testicular, lung, colon, rectum, pancreas, liver, central nervous system, kidney, head, neck, bone, blood, and lymphatic system. In addition to tumor cells, the effector cell can be targeted against auto-antibody producing lymphocytes for treatment of autoimmune disease or an IgE-producing lymphocyte for treatment of allergy. The target can also be microorganism (bacterium or virus) or a soluble antigen (such as rheumatoid factor, or other auto-antibodies and toxins). A microorganism is intended to include pathogens, e.g., viruses, bacteria, fungi, protozoa.

Therefore, the complexes according to the present disclosure may be used in different indications like the treatment of malignant diseases, such as acute myeloid leukemia, allergies, chronic inflammatory diseases, autoimmune diseases, including graft versus host, macrophage activation syndrome, arthritis, rheumatoid arthritis, juvenile arthritis and the elimination of myeloid-derived suppressor cells. In particular, the complexes according to the present disclosure may be used in the treatment of leukemia, neutrophilia, acute and chronic neutrophilic leukaemia (CNL), chronic-myeloid leukemia (CML).

Therefore, the complexes of the present disclosure are suitable for targeting and killing a human CD89 expressing cell (human target cell) comprising a first polypeptide comprising a binding structure for binding the complex to the cellular surface receptor CD89 presented on the cell surface of said human target cell and a second polypeptide comprising a toxic effector domain.

A compound or a substance can be tested for its toxic effect in one or both of the following assays: XTT-based colorimetric cell viability assay (Roehm, N W., et al., J Immunol Methods, 1991, 142: p. 257-) and AnnexinV/PI apoptosis assay (Vermes, I., et al., J Immunol Methods 1995; 184: 39-51).

The "toxic effector domain", here also called "target cell killing domain" comprised in the complex is a peptide or polypeptide that has toxic activity in the targeted cell and may be selected from the group consisting of a human protease, a human serine protease such as granzyme B, a bacteria-originated toxic protein such as the *Pseudomonas aeruginosa* exotoxin A, a human hydrolase such as angiogenin, a human cytoskeleton-associated protein such as the microtubule-associated protein tau, a photosensitizer or a plant-originated toxin such as Ricin A, or variants or functional fragments thereof.

Further examples include ADP ribosylating enzymes like *pseudomonas* exotoxin A, diphteria, cholera-, pertussis- and botulinotoxin and ribosome inactivating proteins like diathin, saporin, bryodin, gelonin, ricin, abrin or restrictocin. Further, ribonucleases (Phosphodiesterases) RNAse H, angiogenin, eosinophil-derived neurotoxin (EDN), eosinophilic cationic protein, onconase and bullfrog lektin. Further examples are prodrug activating enzymes as caliceamicin, glucoseoxidase, carboxypeptidase, alkaline phosphatase, cytosindeaminase, beta-glycosidase, beta-glucoronidase, beta-lactamase, nitroreductase, thymidinkinase or purin-nucleosid phosphorylase. Furthermore, cathepsines, granzymes and combinations and possible variations of the before mentioned protein families. Preferred embodiments are validated toxins as ricin A, alpha sarcin (family of lectins), diphteriatoxin and *pseudomonas* exotoxin A since these toxins are subjects of several clinical studies and their efficacy is well documented. In an advantageous embodiment, the complex according to the present disclosure comprises a second polypeptide selected from the group consisting of *Pseudomonas aeruginosa* exotoxin A (ETA), granzyme B or a variant thereof comprising the substitution R201K (GbR201K, disclosed in EP2758527), angiogenin or a variant thereof comprising the substitution GGRR (Ang GGRR) and microtubule associated protein Tau (MAPtau) as the toxic effector domain.

In some advantageous embodiments, the complexes according to the present disclosure are immunotoxins (ITs) or human cytolytic fusion proteins (hCFP) as described above.

As used herein, the term "immunotoxin" refers to chimeric molecules in which a cell-binding monoclonal antibody or fragments thereof are chemically coupled or genetically fused to a bacterial (e.g. ETA) or plant protein-based toxin (e.g. RT). Immunotoxins per se as well as their constructions are well known to the person skilled in the art.

As used herein, the term "human cytolytic fusion protein" or "hCFP" refers to a completely human immunotoxins in which a cell-binding human ligand or fragments thereof are chemically coupled or genetically fused to a human enzyme (e.g. GranzymeB etc), inhibitory proteins (e.g. MAP) or at least a partial sequence, thereof, the partial sequence having maintained the binding function to a microtubule.

In some further advantageous embodiments, the complexes according to the present disclosure is an Immunotoxin comprising a CD89-specific single-chain variable fragment (scFv) and as the toxic effector domain the *Pseudomonas aeruginosa* exotoxin A (ETA), in particular in particular as a recombinant fusion protein.

The isolated complexes and polypeptides according to the present disclosure are characterized by specific amino acids and is encoded by specific nucleic acid sequences. It will be understood that such sequences include analogues and variants produced by recombinant or synthetic methods wherein such polypeptide sequences have been modified by substitution, insertion, addition or deletion of one or more amino acid residues in the recombinant polypeptides and the complexes according to the present disclosure still are suitable to bind and kill a human cancer cell. Substitutions are preferably "conservative". Substitutions are preferably silent substitutions in the codon usage, which will not lead to any change in the amino acid sequence, but may be introduced to enhance the expression of the protein.

In some advantageous embodiments, the complexes according to the present disclosure comprises as the binding structure for binding the complex to the cellular surface receptor CD89 the amino acid sequence of SEQ ID NO: 1, or homologous polypeptides thereof having an amino acid which is at least 85%, preferably 90%, more preferably 95% identical to the amino acid sequence of SEQ ID NO. 1, which are produced by recombinant or synthetic methods by substitution, insertion, addition or deletion of one or more amino acid residues, or fragments thereof.

In some advantageous embodiments, the complexes according to the present disclosure comprises an amino acid sequence of SEQ ID NO: 2, or homologous polypeptides thereof, which are produced by recombinant or synthetic methods by substitution, insertion, addition or deletion of one or more amino acid residues, or fragments thereof.

In some advantageous embodiments, the complexes according to the present disclosure comprises an amino acid sequence of SEQ ID NO: 3, or homologous polypeptides thereof, which are produced by recombinant or synthetic methods by substitution, insertion, addition or deletion of one or more amino acid residues, or fragments thereof.

In some advantageous embodiments, the complexes according to the present disclosure comprises an amino acid sequence of SEQ ID NO: 4, or homologous polypeptides thereof, which are produced by recombinant or synthetic methods by substitution, insertion, addition or deletion of one or more amino acid residues, or fragments thereof.

In some advantageous embodiments, the complexes according to the present disclosure comprises an amino acid sequence of SEQ ID NO: 5, or homologous polypeptides thereof, which are produced by recombinant or synthetic methods by substitution, insertion, addition or deletion of one or more amino acid residues, or fragments thereof.

Furthermore, the complex according to the present disclosure comprises an amino acid sequence selected from the group consisting of SEQ ID NO: 2, SEQ ID NO: 3, SEQ ID NO: 4 and SEQ ID NO: 5, or homologous polypeptides, variants or mutations thereof having an amino acid which is at least 85%, preferably 90%, more preferably 95% identical to the amino acid sequence of SEQ ID NO. 2, SEQ ID NO. 3, SEQ ID NO. 4 or SEQ ID NO. 5, and that are produced by recombinant or synthetic methods by substitution, insertion, addition or deletion of one or more amino acid residues, or fragments thereof.

"Percent sequence identity", with respect to two amino acid or polynucleotide sequences, refers to the percentage of residues that are identical in the two sequences when the sequences are optimally aligned. Thus, 80% amino acid sequence identity means that 80% of the amino acids in two optimally aligned polypeptide sequences are identical. Percent identity can be determined, for example, by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN14, National Biomedical Research Foundation, Washington, D.C., which adapts the local homology algorithm of Smith and Waterman for peptide analysis.15. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters 5 recommended by the manufacturer and described in the Wisconsin Sequence Analysis Package referred to above. An example of an algorithm that is suitable for determining sequence similarity is the BLAST algorithm, which was described before. Software for performing BLAST analyses is publicly available through the National Center for Biotechnology Information (http://www.ncbi.nlm.nih.gov/). Likewise, computer programs for determining percent homology are also readily available.

The term "mutation" refers to the substitution or replacement of single or multiple nucleotide triplets, insertions or deletions of one or more codons, homologous or heterologous recombination between different genes, fusion of additional coding sequences at either end of the encoding sequence, or insertion of additional encoding sequences or any combination of these methods, which result in a polynucleic acid sequence encoding the desired protein.

Thus, the term "mutations" also refers to all of the changes in the polypeptide sequence encoded by the polynucleic acid sequence modified by one or more of the above-described changes.

The term "variant" means that the amino acid sequence has been modified but retains the same functional characteristics, in particular the binding and destroying effect on human cancer cells. A variant has a sequence identity of at least 70% or preferably at least 80%, 85%, 90%, 95%, 97% or 99% to the parent amino acid sequence.

The term "variant" refers further to a polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or Oalkyl derivatives. The imidazole nitrogen of histidine may be derivatized to form N-im-benzylhistidine. Also included as derivatives are those peptides which contain one or more naturally occurring amino acid derivatives of the twenty standard amino acids. For example: 4-hydroxyproline may be substituted for proline; 5-hydroxylysine may be substituted for lysine; 3methylhistidine may be substituted for histidine; homoserine may be substituted for serine; and ornithine may be substituted for lysine.

The above mentioned fusion proteins may also include on the N-Terminus prior to the single chain sequence: a pelB leader sequence for periplasmic transport, a His$_{10}$-Tag for affinity purification and enterokinase cleavage site allowing removal of tags after use in purification.

To express a fusion protein according to the present disclosure in a recombinant expression system, a DNA encoding the fusion protein or parts thereof, may be inserted into an expression vector such that the gene is operably linked to transcriptional and translational control sequences. In this context, the term "operably linked" means that a protein gene is ligated into a vector such that transcriptional and translational control sequences within the vector serve their intended function of regulating the transcription and translation of the protein gene. The expression vector and expression control sequences are chosen to be compatible with the expression host cell used. The isolated protein domain sequences are typically inserted into the same expression vector. The protein genes are inserted into the expression vector by standard methods. Additionally, the recombinant expression vector can encode a signal peptide that facilitates co-translational translocation of the nascent polypeptide chain into the endoplasmic reticulum (ER). The folded polypeptide (recombinant fusion protein according to this disclosure) may be secreted from a host cell or may be retained within the host cell. Intracellular retention or targeting can be achieved by the use of an appropriate targeting peptide such as C-terminal KDEL-tag for ER retrieval.

In general, those skilled in the art are well able to construct vectors and design protocols for recombinant gene expression. For further details see, for example, Molecular Cloning: a Laboratory Manual: 2nd edition, Sambrook et al., 1989, Cold Spring Harbor Laboratory Press (or later editions of this work) and Current Protocols in Molecular Biology, Second Edition, Ausubel et al. eds., John Wiley & Sons, 1992, which are incorporated herein by reference.

Furthermore, the present disclosure relates to nucleic acid molecules or nucleic acids encoding such a fusion protein as well as to vectors comprising the nucleic acid molecule and host cells comprising a nucleic acid molecule encoding said fusion protein or a vector comprising said vector. The disclosure pertains also to methods of manufacturing said recombinant fusion proteins in a recombinant expression system.

The term "vector" includes a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g. bacterial vectors having a bacterial origin of replication and episomal mammalian vectors). Other vectors (e.g. non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression system" or "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the disclosure is intended to include such other forms of expression vectors, such as viral vectors (e.g. replication-defective retroviruses, adenoviruses and adeno-associated viruses), which serve equivalent functions.

The present disclosure is also directed to a host cell with a vector comprising the recombinant fusion proteins according to the present disclosure. The phrase "recombinant host cell" (or simply "host cell") includes a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

Host cells include progeny of a single host cell, and the progeny may not necessarily be completely identical (in morphology or in total DNA complement) to the original parent cell due to natural, accidental, or deliberate mutation and/or change. A host cell includes a cell transfected or infected in vivo or in vitro with a recombinant vector or a polynucleotide of the present disclosure. A host cell, which comprises a recombinant vector of the disclosure, may also be referred to as a "recombinant host cell".

The term "host cell(s)" refers to cell(s), which may be used in a process for purifying a recombinant protein in accordance with the present disclosure. Such host cells carry the protein of interest (POI). A host cell may also be referred to as a protein-expressing cell. A host cell, according to the present invention, may be, but is not limited to, prokaryotic cells, eukaryotic cells, archaebacteria, bacterial cells, insect cells, yeast, mammal cells, and/or plant cells. Bacteria envisioned as host cells can be either gram-negative or gram-positive, e.g. *Escherichia coli, Erwinia* sp., *Klebsellia* sp., *Lactobacillus* sp. or *Bacillus subtilis*. Typical yeast host cells are selected from the group consisting of *Saccharomyces cerevisiae, Hansenula polymorpha* and *Pichia pastoris*. In some advantageous embodiments, the host cell is a HEK293T cell.

The complex of the present disclosure can be used with a "pharmaceutically acceptable carrier" which includes any and all solvents, dispersion media, coatings, surfactants, antioxidants, preservatives (e.g. antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art.

Therefore, as used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

The complex of the present disclosure can be used with a "pharmaceutically acceptable alst" which includes any salt that retains the desired biological activity of the parent compound and does not impart any undesired toxicological effects (see e.g., Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

The actual dosage amount of a complex or composition of the present disclosure administered to a subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

A complex composition of the present disclosure can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

To administer a complex or composition of the present disclosure by certain routes of administration, it may be necessary to coat the complex compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al. (1984) J Neuroimmunol. 7:27).

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drag concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals. Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Actual dosage levels of the active ingredients in the pharmaceutical compositions of the present disclosure may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of compositions of the invention will be that amount of the compound which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of therapeutic compositions may be administered as two, three, four, five, six or more sub-doses administered separately at appropriate intervals throughout the day, optionally, in unit dosage forms. While it is possible for a compound of the present * invention to be administered alone, it is preferable to administer the compound as a pharmaceutical formulation (composition).

In advantageous embodiments, recombinant human cytolytic fusion proteins according to the disclosure are used for treating a malignant disease, an allergy, autoimmune disease, tissue rejection reaction, or chronic inflammation reaction.

Further embodiments of the present disclosure pertain to polypeptides suitable for the detection of CD89, wherein said polypeptide comprises the amino acid sequence of SEQ ID NO: 1, or a homologous polypeptide, variant or mutation thereof having an amino acid which is at least 85%, preferably 90%, more preferably 95% identical to the amino acid sequence of SEQ ID NO. 1, which are produced by recombinant or synthetic methods by substitution, insertion, addition or deletion of one or more amino acid residues, or fragments thereof.

In further embodiments, homologous polypeptides, variants or mutations of said polypeptides suitable for the detection of CD89 shows a sequence identity of at least 70% or preferably at least 80%, 85%, 90%, 95%, 97% or 99% to the parent amino acid sequence.

In some examples, the polypeptides are coupled to a detectable label like an affinity label. As used herein, the term "affinity label" refers to a substance, molecule or biomolecule, which is coupled to the polypeptides suitable for the detection of CD89 to form a "fusion tag" or a "affinity tag", by a means, e.g., expression, and which is further capable of specifically binding to a fluorescent label. In particular, the fusion tag is a fusion tag protein. Examples of the fusion tag proteins are SNAP-tags, CLIP-tags, Lumio tags, or HaloTags.

In some embodiments, the detectable CD89-protein is presented on a human target cell or a fragment thereof like parts of the cell membrane of a disrupted target cell.

In further embodiments, the present disclosure pertains to a method for the detection of CD89 contained in a sample, comprising:

(a) contacting a sample with a polypeptide suitable for the detection of CD89 as described in the present disclosure and with fusion tag specific fluorophores that specifically bind the fusion tags coupled to said polypeptide; and (b) detecting the presence of CD89 in the sample by fluorescence signals associated with the fusion tag specific fluorophores.

As used herein, the terms "fluorescent label", "fluorophore", "dyes", and "fluorescent molecule" may have the same or similar meaning in the invention and are interchangeable throughout the invention. For example, the term "fluorophore", "fluorochrome", or "chromophore", as used herein, refers to a fluorescent chemical compound that can re-emit light upon light excitation. Fluorophores may typically contain several combined aromatic groups, or plane or cyclic molecules with several ii bonds.

Fluorophores may sometimes be used alone, as a tracer in fluids, as a dye for staining of certain structures, as a substrate of enzymes, or as a probe or indicator (when its fluorescence is affected by environment such as polarity, ions, et. al.). But more generally fluorophore may be covalently bonded to a macromolecule, serving as a marker (or dye, or tag, or reporter) for affine or bioactive reagents (antibodies, peptides, nucleic acids, et. al.). Fluorophores may notably be used to stain tissues, cells, or materials in a variety of analytical methods, i.e. fluorescent imaging and spectroscopy.

The affinity tag may be any molecules or biomolecules which are capable of specifically linking to one fluorescent molecule as the fluorophore (fluorescent label). Specifically, the affinity tag may be proteins having suicidal enzymatic activity, also called suicide enzymes. Suicide enzymes are proteins whose enzymatic activity is modified by specific mutations allowing them to bind a substrate rapidly, covalently, and irreversibly, as these enzymes can each bind only one fluorescent molecule, and the further binding activity of the enzyme is blocked by the binding of the substrate.

The fluorophore or fluorescent label may be any fluorescent molecules or dyes. Specifically, the fluorophore or fluorescent label may be a dye compatible with the fluorescent detection equipment being used. Some examples of these dyes may be seen below. All of these dyes may be commercially available as fluorescent substrates for fusion tags, and each binds covalently to a different tag. Most developed fusion tags may have many fluorescent variations of the ligand to cover a broad portion of the UV spectrum. Any suitable fluorescent molecules or dyes may be used for the present invention. In a preferred embodiment of the present invention, a microfluidic system such as LabChip systems (available from Caliper) may be equipped with a 635 nm excitation light source, and a 700 nm emission filter, making dyes with excitation and emission maxima near these wavelengths ideal choices when selecting a fluorophore for use on a LabChip system. Any fluorescent molecules or dyes having suitable excitation and emission maxima near the required wavelength may be used for the present invention.

In advantageous embodiments of the present disclosure, the polypeptides suitable for the detection of CD89 as described in the present disclosure can be used for the diagnosis of CD89+ malignancies. The diagnosis may be in vivo or ex vivo. Therefore, the present disclosure pertains also to methods for the diagnosis of CD89+ malignancies, comprising administering to a patient a polypeptide suitable for the detection of CD89 as described in the present disclosure or contacting a biological sample taken from a patient with a polypeptide suitable for the detection of CD89 as described in the present disclosure.

Advantageous embodiments refers to methods of detecting the presence of CD89 or a cell expressing CD89 in a sample, comprising: contacting the sample with the polypeptides suitable for the detection of CD89 as described in the present disclosure under conditions that allow for formation of a complex between the polypeptide and CD89; and detecting the formation of the complex.

Further embodiments of the present disclosure relate to methods for detecting in vitro or in vivo the presence of CD89 in a sample, e.g., for diagnosing a CD89-related disease. In one embodiment, this is achieved by contacting a sample to be tested, optionally along with a control sample, with a polypeptide suitable for the detection of CD89 as described in the present disclosure under conditions that allow for formation of a complex between the polypeptide and CD89. Complex formation is then detected (e.g. using an ELISA). When using a control sample along with the test sample, complex is detected in both samples and any statistically significant difference in the formation of complexes between the samples is indicative the presence of CD 89 in the test sample.

The following methods and examples are offered for illustrative purposes only, and are not intended to limit the scope of the present disclosure in any way.

EXAMPLES

It should be understood that the following examples are for illustrative purpose only and are not to be construed as limiting this disclosure in any manner. All publications, patents, and patent applications cited herein are hereby incorporated by reference in their entirety for all purposes.

For specific targeting and killing, a complex (recombinant fusion protein) was constructed comprising an anti-human CD89 single chain fragment variable (scFv) and the *Pseudomonas* exotoxin A (ETA').

Furthermore, human cytolytic fusion proteins (hCPs) were generated by fusing the CD89-specific scFv to human derived effect domains like a granzyme B variant comprising the substitution R201K (GbR201K, disclosed in EP2758527), a angiogenin variant GGRR (Ang GGRR) (Cremer, C., et al., Journal of Immunotherapy, 2014) or microtubule associated protein Tau (MAPtau).

In the following examples it was shown that FcαR (CD89) is expressed by a subset of leukaemic cells and can be used not only as a diagnostic marker but also as a novel immunotherapeutic target. It was demonstrated that a CD89-specific fusion proteins can eliminate myeloid cell lines derived from different AML subtypes in vitro, as well as AML and CMML cells ex vivo.

The abundance of CD89 on AML-derived cell lines and primary cells from AML and CMML patients was described. CD89 is a suitable immunotherapeutic target for haematological malignancies because it is not found on pluripotent stem cells or CD34+ hematopoietic progenitor cells, so the homeostasis of normal FcαR+ immune effector cells and the recovery of the haematopoietic system after therapeutic intervention remains unaffected. Earlier immunotherapeutic approaches for the treatment of myeloid malignancies include Gemtuzumab-ozogamicin (GO), a humanised CD33-specific monoclonal antibody (mAb) chemically coupled to the cytostatic drug calicheamicin (Albo, C., et al. Haematologica, 2004, 89(7): p. 845-851). GO was withdrawn from the market in 2010 because only limited efficacy was demonstrated in clinical trials. Nevertheless, GO showed promising results in recent clinical phase II-III studies, underlining its importance as an alternative in AML therapy. In addition to this antibody-drug conjugate (ADC), a variety of recombinant immunotherapeutic agents, such as bispecific/trispecific scFv, T-cells with chimeric antigen receptors (CARs), and ITs, are currently under investigation. Here we focused on the generation and characterisation of a recombinant, scFv-based IT and hCFPs specific for CD89. One advantage of scFvs over full size mAbs is the lack of the Fc region. Hence, scFvs show a reduced immunogenicity and no binding to Fc-receptor expressing cells, which thereby avoids the rapid clearance of the ITs. Several recombinant ETA'-based ITs have been developed over the last decade, targeting and eliminating a variety of myeloid malignancies including CD7+, CD33+, CD64+ and CD123+ cells (Gasiorowski, R E. et al., Br J Haematol, 2014, 164: p. 481-95, Monnier, P., et al., Antibodies, 2013, 2: p. 193-208, Schwemmlein, M., et al., Br J Haematol, 2006, 133: p. 141-151, Stein, C., et al., Br J Haematol, 2010, 148: p. 879-889, Thorpe, S. J., et al., Scand J Immunol 2003, 57: p. 85-92, Tur, M K., et al., Cancer Res, 2003; 63: p. 8414-9). In addition different hCFPs specific for the elimination CD64+ target cells and myeloid malignancies were already described in literature (Schiffer, S., et al., Int J Cancer, 2014, 135: p. 1497-508, Hristodorov, D., et al., Br J Cancer, 2013, 109: p. 1570-8, Cremer, C., et al., Journal of Immunotherapy, 2014).

In the present disclosure the construction of a CD89 (scFv)-ETA' IT and the successful in vitro and ex vivo elimination of cells derived from different AML subtypes and myeloid malignancies, respectively, is shown for the first time.

1. Cloning and Expression of CD89(scFv)-fusion Proteins

The open reading frame (ORF) for the anti-human CD89 (scFv) (Guettinger, Y., et al., J Immunol, 2010, 184: p. 1210-1217) was capped with 5' SfiI and 3' NotI restriction sites using adapted PCR primers and the product was ligated into the pMT vector, already containing the ETA' sequence using the SfiI and NotI sites. (Berges, et al 2014) The plasmid was cloned in *Escherichia coli* strain DH5α(New England Biolabs, UK) and successful cloning was confirmed by test digestion and sequencing. The CD89(scFv)-ETA' fusion protein was expressed in *E. coli* strain BL21 (DE3), purified and characterised as previously described for H22 (scFv)-ETA' (Ribbert, T., et al., Br J Dermatol, 2010; 163: p. 279-86, Tur, M K., et al., Cancer Res, 2003; 63: p. 8414-9).

For the human cytolytic fusion proteins (hCFPs) the CD89(scFv) was transferred from the pMT vector system, described above, into the pMS vector system using the cloning SfiI and NotI as restriction sites. The pMS vector template was containing the sequence of the effector protein: a microtubule-associated protein tau (MAPtau), a mutant of angiogenin (Ang GGRR) or a mutant form of granzyme B (EGbR201K). Analogously to CD89(scFv)-ETA', the successfully cloned constructs were transformed into *E. coli* DH5α and the sequences of the constructs were verified by sequencing. The expression of the pMS based constructs (CD89(scFv)-Ang GGRR, CD89(scFv)-MAPtau and EGbR201K-CD89(scFv) was carried out transiently in HEK293T cells as previously described by Stocker, et al. The purification and characterization procedures were conducted as described for CD89(scFv)-ETA'.

Construction, Expression and Binding Characteristics of the Fusion Protein CD89(scFv)-ETA'

Figure 3:
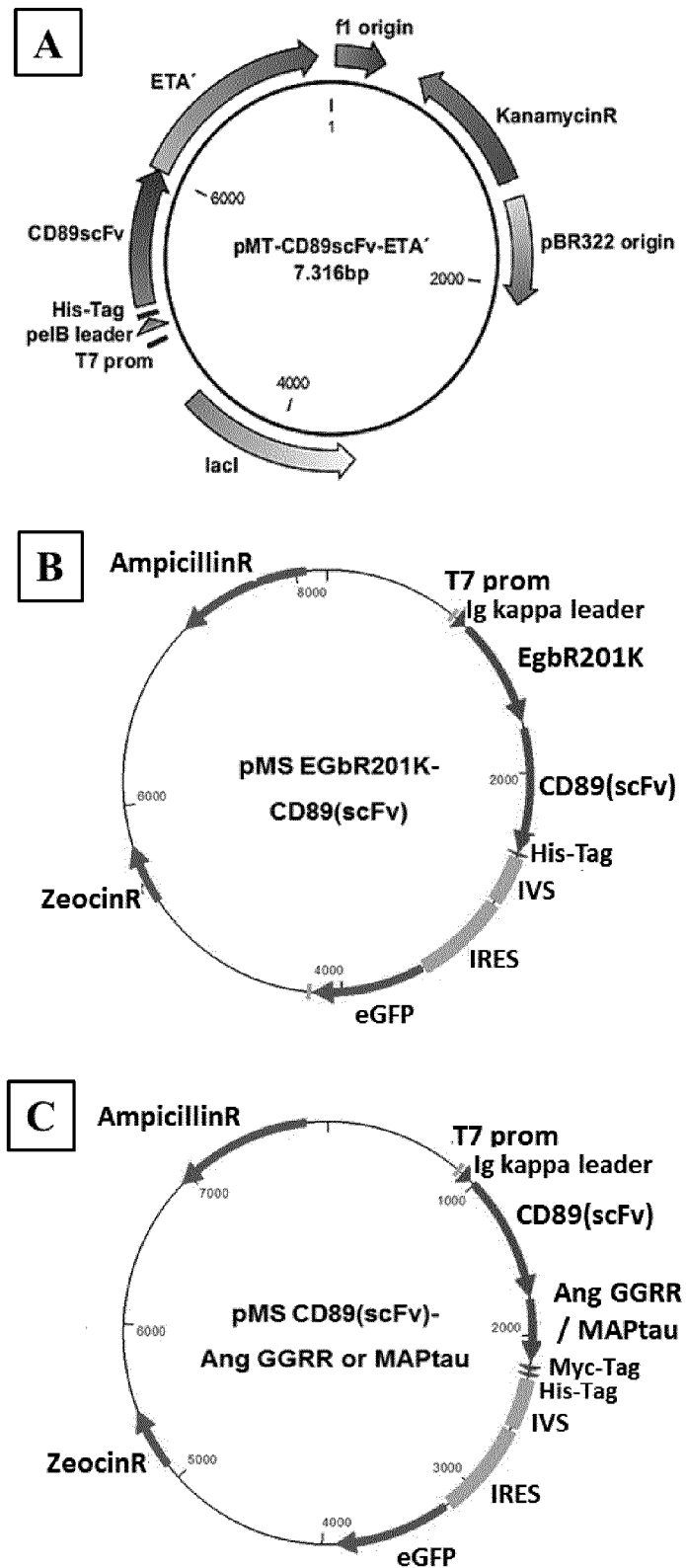
FIG. 3 (A) shows the design of the CD89(scFv)-ETA' vector. PelB, leader sequence for periplasmic transport; His-Tag, polyhistidine tag; CD89(scFv), single chain variable fragment comprising the VL and VH sequences separated by a (G4S)4 linker; ETA', truncated version of Pseudomonas exotoxin A containing domains Ib, II and III.
Figure 4:
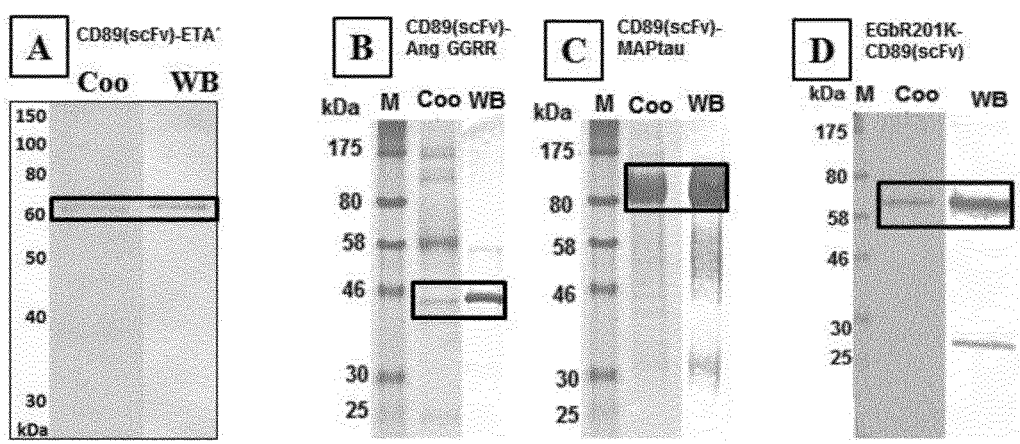
FIG. 4 (A) shows a SDS-polyacrylamide gel. CD89-ETA' was eluted from a Ni/NTA matrix followed by size exclusion and buffer exchange to PBS. Left lane shows SDS-polyacrylamide gel stained with Coomassie Brilliant Blue (Coo). Right lane shows corresponding western blot (WB) probed with a mouse anti-ETA' primary mAb (TC1) and an AP-conjugated goat anti-mouse secondary mAb.

We generated a fusion of a CD89-specific scFv derived from the humanised full-size anti-human CD89 mAb A77, to the truncated toxin ETA' (FIG. 3 (A)). The recombinant IT was expressed in bacteria and purified by affinity chromatography targeting the $His_6$ tag, achieving a yield of 3 ring/1 culture supernatant with purity greater than 90% as determined by SDS-PAGE and staining with Coomassie Brilliant Blue. The identity of the recombinant protein was confirmed by western blot using an ETA'-specific mAb. Under denaturing conditions, SDS-PAGE revealed a band with the expected molecular weight of approximately 70 kDa (FIG. 4 (A)). The hCFPs consisting of the CD89-specific scFv and a human effector domain (GbR201K, Ang GGRR or MAPtau) were generated and expressed transiently in HEK293T cells. The purification was carried out as described for CD89scFv-ETA' and yields up to 640 µg/l were achieved. The identity of the fusion proteins was verified by specific detection using an anti-poly-histidin antibody on the western blot. The theoretical mass of CD89(scFv)-Ang GGRR is 46.8 kDa, of EGbR201K-CD89 (scFv) is 58.8 kDa and of CD89(scFv)-MAPtau is 80 kDa and bands of this sizes were detected on coomassie-stained denatured SDS-PAA gel and on the corresponding western blot membrane (FIGS. 4 (B), (C) and (D)).

2. Patient Samples and Cell Lines

AML cell lines HL-60 (FAB, AML M2; DSMZ no. ACC 3), Mono-Mac-1 (FAB, AML M5; DSMZ no. ACC 252), THP-1 (FAB, AML M5 (Martino, et al 2006), DSMZ no. ACC 16), the histiocytic lymphoma cell line U937 (DSMZ no. ACC 5), and the Burkitt lymphoma cell line Ramos (DSMZ no. ACC 603) were grown in standard RPMI 1640 medium (Invitrogen) supplemented with 10% (v/v) foetal calf serum (BioChrom), 50 µg/ml penicillin and 100 µg/ml streptomycin (Gibco) at 37° C., 5% $CO_2$ and 100% humidity. The cells were stimulated with either IFNγ or TNFα for 24 h prior to flow-cytometry and cytotoxicity assays. Primary mononuclear cells were isolated by density gradient centrifugation using Biocoll separating solution (Biochrom AG). The cells were isolated from the peripheral blood of pre-treatment leukaemia patients (diagnosis based on the WHO classification is shown in Table 1), after receiving informed consent and with the approval of the Clinical Research Ethics Board of the University of Aachen. Cells from AML CMML patients were cultivated under the conditions described above.

3. Analysis of CD64 and CD89 Expression and Receptor Density

The expression of CD64 and CD89 in the different cell lines was analysed by flow cytometry. Cells were incubated with a 150 ng fluorophore-labelled mAb in PBS (pH 7.4) containing 2 mM EDTA and 1% (w/v) human blocking serum (BioChrom) for 30 min on ice followed by two washing steps with PBS. CD64 was blocked with 50 nM of the H22(scFv) antibody fragment (Hristodorov, D., et al., MAbs, 2014, 6: p. 1283-1289). The fluorescence was then analysed on a FACSCalibur™ flow cytometer (Becton Dickinson). The following antibodies were used for detection: mouse anti-human CD64 [10.1]:APC (eBioscience) and mouse anti-human CD89 [MIP8]:FITC (AbD Serotec). The number of CD89 and CD64 molecules expressed on the cell surface was determined using the Qifikit® (Dako). Flow cytometry was carried out according to the manufacturer's protocol using mouse anti-human CD64 [10.1]:PE, mouse anti-human CD89[A59]:PE, goat anti-mouse IgG [Poly4053]:PE and a mouse IgG1:PE isotype control mAb, all purchased at Biolegend. All experiments were carried out in triplicates.

Confirmation of CD64 and CD89 Expression and Receptor Density in AML Cell Lines

The expression levels of CD64 and CD89 in different AML cell lines were estimated using double staining to determine the number of cells expressing CD64 and CD89 under normal conditions and after stimulation with IFNγ or TNFα. The expression of CD64 and CD89 was detectable on all AML cell lines (HL-60>90%; Mono-Mac-1>30% and THP-1>25%) under normal conditions and in the presence of IFNγ and TNFα(FIG. 1). Strong upregulation was observed in the presence of TNFα, which increased the numbers of $CD64^+$ and $CD89^+$ cells to >80% in all the AML cell lines. The expression profile of the two receptors in the histiocytic cell line U937 was investigated. CD89 was detected on the cell surface under normal conditions (~52%) and after stimulation (IFNγ ~24% and TNFα ~35%). CD64 or CD89 were not detected on Burkitt lymphoma Ramos cells.

Figure 2:
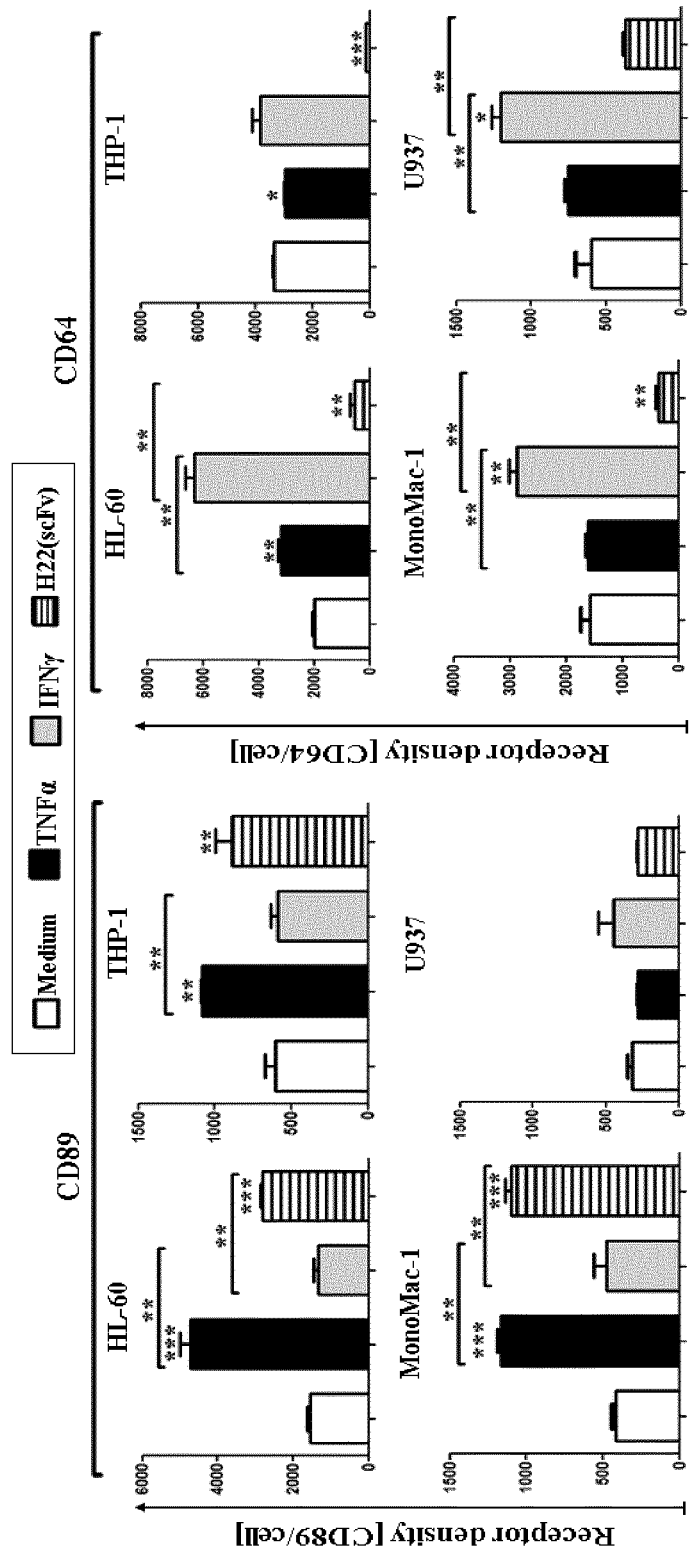
FIG. 2 are diagrams showing CD89 and CD64 density on human AML and U937 histiocytic lymphoma cells. HL-60, THP-1, Mono-Mac-1 and U937 cells were incubated with medium only or stimulated with either 100 U/ml IFNγ or 1000 U/ml TNFα for 24 h prior to measurement. The AML cells were incubated with PE-labelled detection antibodies in PBS with 1% (v/v) blocking human serum. The MFI signal of bound antibodies was measured using a FACSCalibur™ flow cytometer. The receptor density was estimated using calibration beads from the Qifikit® and a goat anti-mouse IgG1 mAb:PE.

The expression levels of CD89 and CD64 were determined using the Qifikit® showing that receptor expression was clearly stimulus-dependent. Neither the growth medium nor the presence of IFNγ influenced the abundance of CD89, which ranged from less than 1000 receptors on the surface of Mono-Mac-1 and THP-1 cells up to ~1500 receptors on the surface of HL-60 cells (FIG. 2). However, these levels increase 2-3-fold in all cell lines in the presence of 5000/mL TNFα. The stimulus of 1000/ml IFNγ could clearly induce CD64 surface expression reaching up to 6500 receptors for HL-60 cells and around 3000 receptors for Mono-Mac-1 and THP-1 cells (FIG. 2). Potential interactions between CD64 and CD89 were investigated by treating the cells with the CD64-specific antibody fragment H22(scFv), which selectively binds to and blocks CD64 without activating it (Hristodorov, D., et al., MAbs, 2014, 6: p. 1283-1289). This treatment induced the expression of CD89 on the surface of all cell lines except U937, where the abundance remained at fewer than 500 receptors per cell regardless of the stimulus. The TNFα-induced upregulation of CD89 surface expression was similar to the IFNγ-dependent upregulation of CD64 surface expression, and the specific blocking activity of H22(scFv) was also confirmed.

4. Cell-Binding Analysis by Flow Cytometry

We incubated $5 \times 10^5$ cells with 100 ng CD89(scFv)-ETA' and 500 ng CD89(scFv)-fusion proteins in PBS (pH 7.4) containing 2 mM EDTA and 0.5% (w/v) bovine serum albumin for 30 min on ice, followed by two washes with PBS. The cells were then incubated with 0.125 ng of an anti-$His_5$-Alexa Fluor 488 mAb (Qiagen) for 30 min on ice in the dark before two further washes with PBS.

Binding Confirmation of CD89-targeting Fusion Proteins

Figure 5:
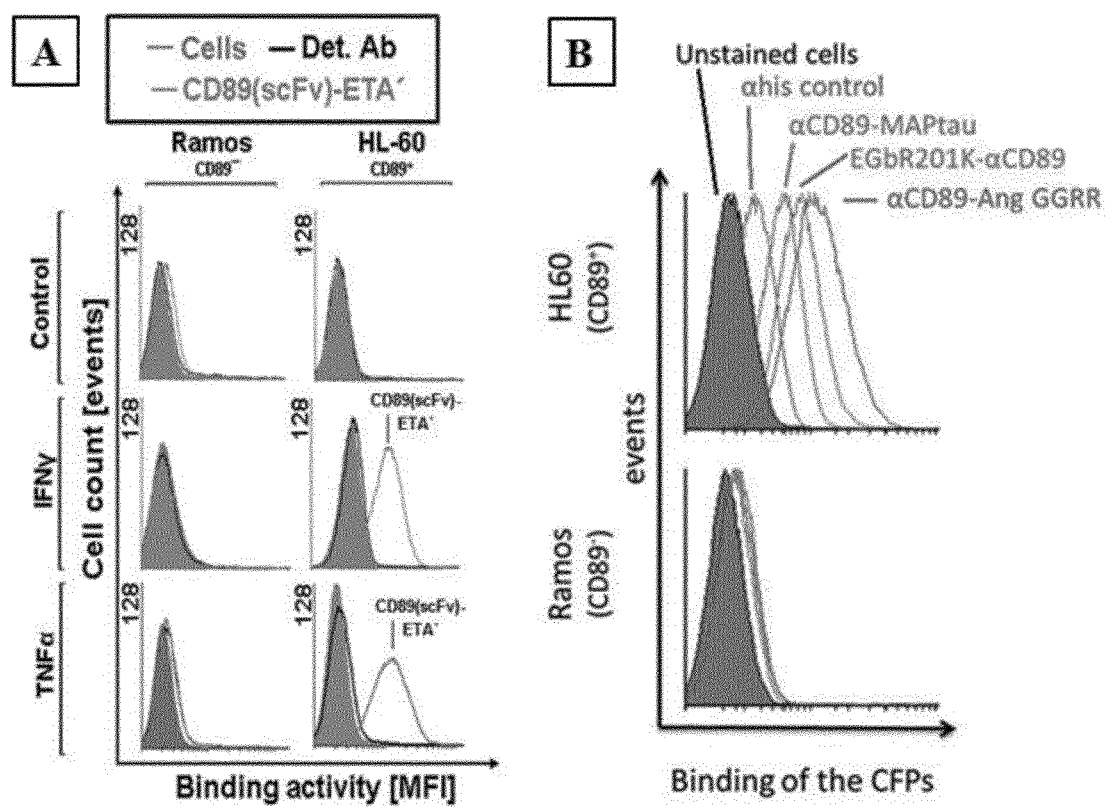
FIG. 5 (A) is a diagram showing the specific binding of the CD89(scFv)-ETA' to unstimulated CD89+ HL-60 and CD89– Ramos cells, and the same cells stimulated with 100 U/mL IFNγ or 1000 U/ml TNFα, analysed by flow cytometry with a Alexa488 coupled mouse anti-polyhistidine mAb.

The cell-binding activity of purified CD89(scFv)-fusion proteins was examined by flow cytometry and could be successfully proven as indicated in FIG. 5. Additionally, CD89(scFv)-ETA' also bound specifically to the $CD89^+$ AML M5 cell lines Mono-Mac-1 and THP-1, and the histiocytic cell line U937 (data not shown).

5. In Vitro Functionality of CD89(scFv)-Ang GGRR and GbR201K-CD89(scFv)

The RNase assay was performed to examine the in vitro functionality of the CD89(scFv)-Ang GGRR fusion protein. Therefore different concentrations of the protein were incubated with 600 ng yeast tRNA in assay buffer (30 mM Tris-HCl buffer (pH 7.5) containing 30 mM NaCl) for 1.5 h at 37° C. As positive control 100 ng of RNase A were used and as negative control the tRNA was incubated with RNase free Tris-HCl sample buffer (pH 7.5). The reaction was stopped by adding the 6× loading dye (48% (v/v) formaldehyde, 48% (v/v) glycerin, 0.25% (v/v) bromophenol blue, 20 mM sodium phosphate (pH 7.5)) in a dilution of 1:6. Afterwards the degradation of tRNA was analyzed using a RNase free 1% agarose gel at 100V for 7 min and the bands were visualized by UV illumination.

The activity of GbR201K-CD89(scFv) after enterokinase digestion was detected by cleavage of 200 µM of the colorimetric, synthetic substrate Ac-IETD-pNA (Calbiochem/Merck, Darmstadt) which mimics the cleavage site of pro-caspase 3. A granzyme B standard was used as positive control and was applied in a concentration of 90 ng. For the negative control assay buffer (100 mM NaCl, 50 mM HEPES, 10 mM DTT, 1 mM EDTA, 10% (v/v) glycerin, 0.1% (w/v) CHAPS, pH 7.4) was incubated with the substrate. The reaction was monitored in 96-well plates in a microplate reader at 405 nm and 37° C. at 2 min intervals for 1 h. Afterwards, time was plotted against the absorbance so differences in activity could be evaluated.

Confirmation of Functionality of CD89(scFv)-Ang GGRR and GbR201K-CD89(scFv)

Figure 6:
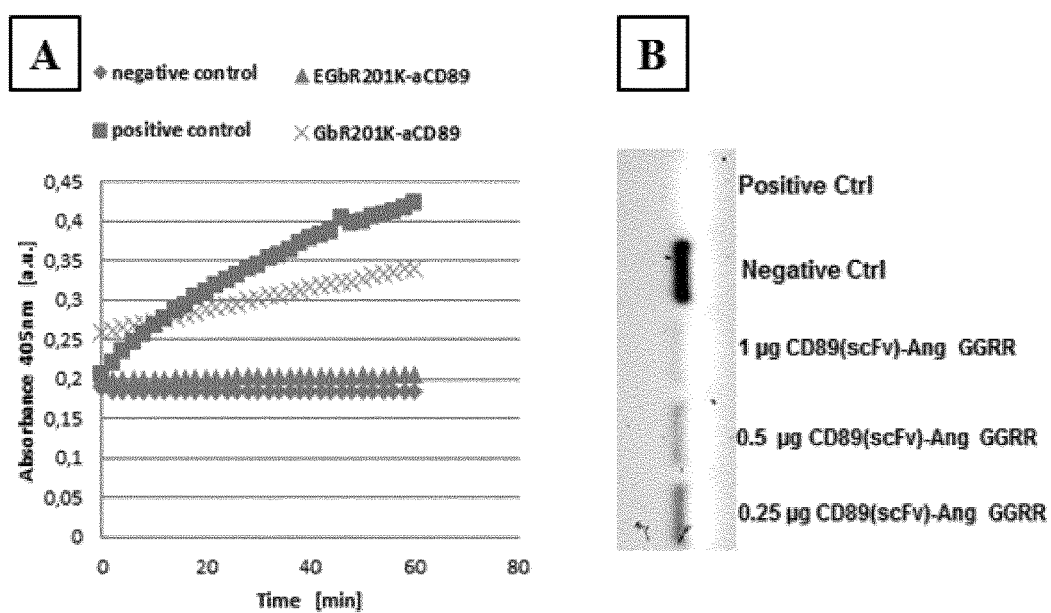
FIG. 6 (A) indicates the enzymatic activity of EGbR201K-CD89(scFv) and the enterokinase digested version—GbR201K-CD89(scFv). The proteolytic activity of activated protein was measured via the described colorimetric assay based on the synthetic granzyme B substrate Ac-IETD-pNA. The kinetic was documented for 1 h with a 2 min interval at 37° C. and 405 nm in an ELISA plate reader.

We could confirm the RNase activity of the fusion protein. A concentration dependent degradation of the tRNA was detected, whereas 1 µg, 500 ng and 250 ng of applied CD89(scFv)-Ang GGRR reduced the UV-signal of the used tRNA to 15%, 25% and 50%, respectively (FIG. 6 (B)).

The activity of the granzyme B part of GbR201K-CD89 (scFv) was confirmed by the increasing absorbance over time course using the described above colorimetric kinetic measurement (FIG. 6 (A)).

6. Apoptosis Assay

An Annexin V/propidium iodide (PI) assay was used to measure the pro-apoptotic activity of CD89(scFv)-ETA'. We incubated $5 \times 10^5$ cells per ml with different concentrations of CD89(scFv)-ETA' in a 24-well plate (Greiner, Germany) for 72 h at 37° C., 5% $CO_2$ and 100% humidity. Ramos cells (CD89−) were used as a control. After incubation, the cells were washed twice with PBS (pH 7.4) and stained with Annexin V-FITC (eBioscience) in Annexin V binding buffer (10 mM HEPES/NaOH, pH 7.4, 140 mM NaCl, 2.5 mM $CaCl_2$) for 30 min at room temperature in the dark. Finally, the cells were washed as described above, resuspended in Annexin V buffer containing 10 µg/ml PI and analysed by flow cytometry.

Antigen-specific Dose-dependent In Vitro Cytotoxicity of CD89-fusion Proteins

Figure 7:
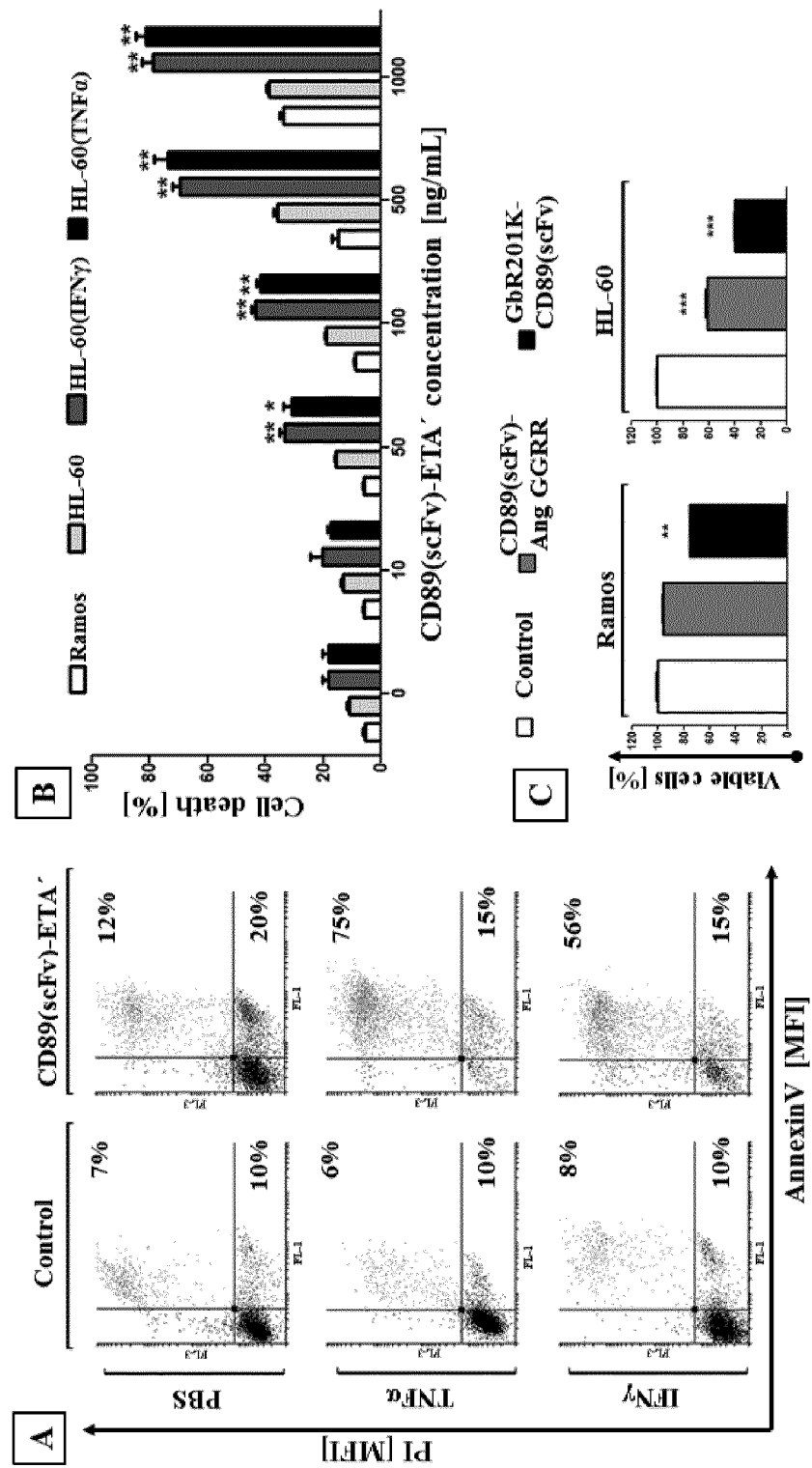
FIG. 7 shows the cytotoxicity of CD89(scFv)-fusion proteins against HL-60 cells. Cytotoxicity assays were carried out by incubating with CD89(scFv)-fusion proteins with unstimulated HL-60 cells or the same cells stimulated with either IFNγ or TNFα. (A) Dot plots of Annexin V/PI stained HL-60 cells (100 U/ml IFNγ or 1000 U/ml TNFα) after incubation with either PBS as control or 15 nM (~1 μg/ml) CD89(scFv)-ETA'.

The cytotoxic effector proteins included in ITs should preferably induce apoptosis rather than necrosis or pyroptosis because the former does not cause undesirable inflammatory responses. The ability of CD89(scFv)-ETA' to induce apoptosis in the different AML cell lines was therefore tested by double staining with Annexin V and PI after treatment for 72 h. Accordingly, CD89(scFv)-ETA' triggered apoptosis in HL-60 cells regardless of the presence or nature of stimulation but did not affect CD89− Ramos cells. Quantitative experiments confirmed a dose-dependent relationship, i.e. greater concentrations of CD89(scFv)-ETA' increased the efficiency of apoptosis in HL-60 cells regardless of the presence or nature of stimulation (FIGS. 7 (A) and (B)), and the cytotoxic activity of CD89(scFv)-ETA' was similar to that previously described for Ki4(scFv)-ETA and H22(scFv)-ETA' under comparable conditions (Barth S., et al., Applied and environmental microbiology, 2000, 66: p. 1572-9; Barth S., et al., Blood 2000, 95: p. 3909-14). The cytotoxic effect of CD89(scFv)-Ang GGRR and GbR201K-CD89(scFv) could be estimated to 40% and 60%, respectively, (FIG. 7 (C)).

Antigen-specific Pro-apoptotic Activity of CD89(scFv)-ETA'

Figure 9:
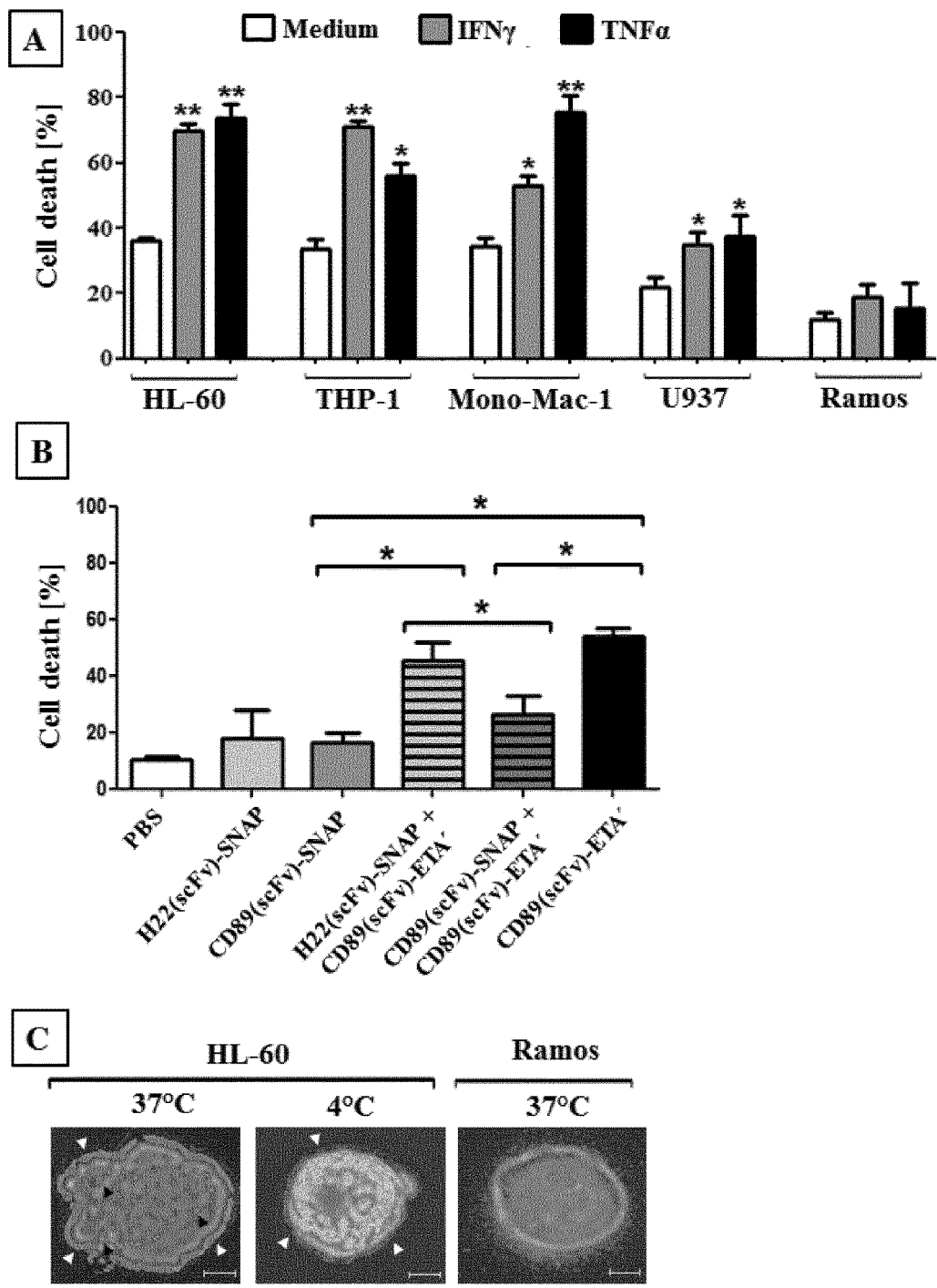
FIG. 9 shows the cytotoxicity of CD89(scFv)-ETA' is antigen-specific and depends on internalisation. Cell death is shown as the sum of early and late apoptotic/necrotic cells measured by Annexin V/PI staining. (A) An apoptosis assay was carried out using 10 nM (~700 ng/ml) CD89(scFv)-ETA' to treat unstimulated cancer cells and the same cells stimulated with 100 U/mL IFNγ or 1000 U/ml TNFα. The number of dead cells was determined after 72 h exposure to the IT. (B) Induction of apoptosis by 10 nM CD89(scFv)-ETA' in TNFα-stimulated HL-60 cells (1000 U/ml) was only blocked by the addition of a 50-fold molar excess of CD89(scFv)-SNAP and not with the control H22(scFv)-SNAP. (C) Confocal microscopy of stimulated HL-60 cells (1000 U/mL TNFα) after incubation with 50 nM CD89 (scFv)-SNAP-BG-Vista® Green at 37° C. and 4° C. CD89$^-$ Ramos cells were used as a negative control. Internalisation was analysed after 30 min incubation. White and black arrows indicate surface binding and internalisation, respectively. Bar=1 μm.

We also investigated the rate of IT-mediated cell death in other AML cell lines and in U937 histiocytic lymphoma cells (FIG. 9 (A)). The statistical significance of antigen-dependent CD89(scFv)-ETA' cytotoxicity was confirmed using a competition assay. A dose-dependent reduction in cytotoxicity was demonstrated in the presence of a 50-fold molar excess of CD89(scFv) fused to the non-toxic SNAP protein (Amoury, et al 2013). Neither a non-specific ETA' fusion protein containing the CD30-specific Ki4(scFv) (Barth S., et al., Blood 2000, 95: p. 3909-14) (data not shown) nor SNAP fused to either CD89(scFv) or H22(scFv) showed evidence of cytotoxicity against the cell lines we tested (FIG. 9 (B)).

Ex Vivo Cytotoxicity Towards CD89+ Leukaemia Cells

Figure 10:
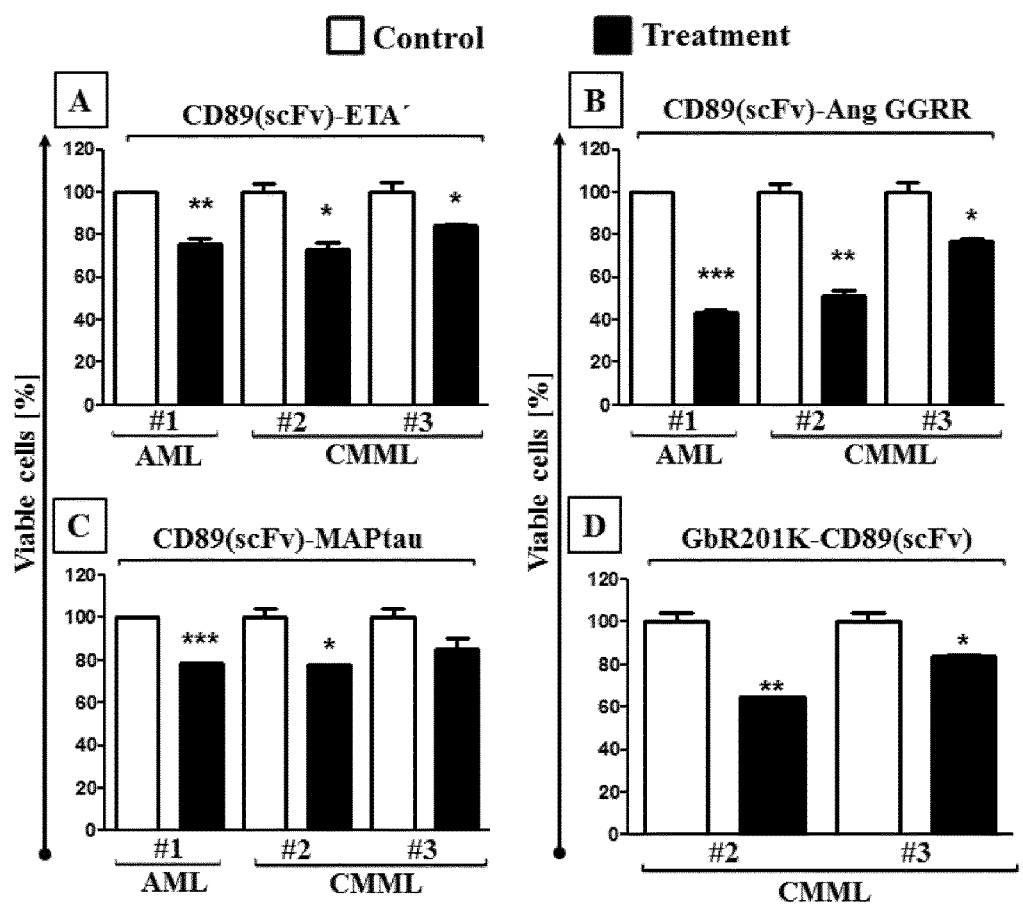
FIG. 10 shows the efficient CD89(scFv)-targeted killing of CD89+ primary leukaemia cells using described CFPs. Primary mononuclear cells derived from peripheral blood of leukaemia patients were incubated with 200 nm fusion protein for 13 hours at 37° C. The pro-apoptotic effect of CD89(scFv)-ETA' (A), CD89(scFv)-Ang GGRR (B), CD89 (scFv)-MAPtau (C) and GbR201K-CD89(scFv) (D) was measured using an Annexin V/PI staining. The number of viable cells was estimated by counting Annexin V/PI-negative cells, and the untreated control was normalised to 100%. Data represent mean values with standard deviations of duplicates. Statistical significance was determined via two-tailed unpaired Student's t-test, (*): $p<0.05$, : $p<0.01$, (*): $p<0.001$.

Primary cells obtained from three patients diagnosed with three different forms of myeloid leukaemia were tested: (#1) AML and (#2, #3) CMML. The isolated primary cells were tested for the presence of CD89 and we found the percentage of positive cells was 75% for the AML patient and 69% and 73% for both CMML patients (Table 1). We monitored apoptosis induced by CD89(scFv)-ETA', CD89(scFv)-Ang GGRR, GbR201K-CD89(scFv) and or CD89(scFv)-MAPtau using the Annexin V/PI staining assay (FIG. 10). The number of viable cells was reduced when all three samples of primary cells were treated with each fusion proteins. Annexin V staining indicated an CD89(scFv)-ETA'IT-mediated cytotoxic effect resulting in the elimination of ~25% AML, ~25% CMML #2 and ~20% CMML #3 primary cells (FIG. 10 (A)). Furthermore, CD89(scFv)-Ang GGRR could eliminate ~60% of AML, ~50% CMML #2 and ~25% of CMML #3 primary cells (FIG. 10 (B)). CD89 (scFv)-MAPtau resulted in an elimination ~20% AML, ~20% CMML #2 and ~15% CMML #3 primary cells (FIG. 10 (C)) and GbR201K-CD89(scFv) showed a cytotoxic effect by eliminating ~35% CMML #2 and ~15% CMML #3 primary cell (FIG. 10 (D)).

7. Colorimetric Cell Proliferation Assay

The cytotoxic effect of the different ITs and hCFPs was determined by measuring the conversion of XTT to a water-soluble orange formazan dye. (Roehm, et al 1991) We seeded $5 \times 10^5$ cells/well into a 96-well microtitre plate and incubated them with different dilutions of the recombinant protein for 72 h at 37° C., 5% $CO_2$ and 100% humidity. We added 50 µl 100:1 XTT/phenanzinemethosulfate (Serva and Sigma-Aldrich) to each well and incubated the plates for 2-4 h. The absorbance at 450-630 nm was measured using an Epoch Microplate Spectrophotometer (Biotek). Data were normalised by setting the 100% and 0% values to cells treated with 10 µg/ml zeocin and untreated cells, respectively. All experiments were carried out in triplicates.

Figure 8:
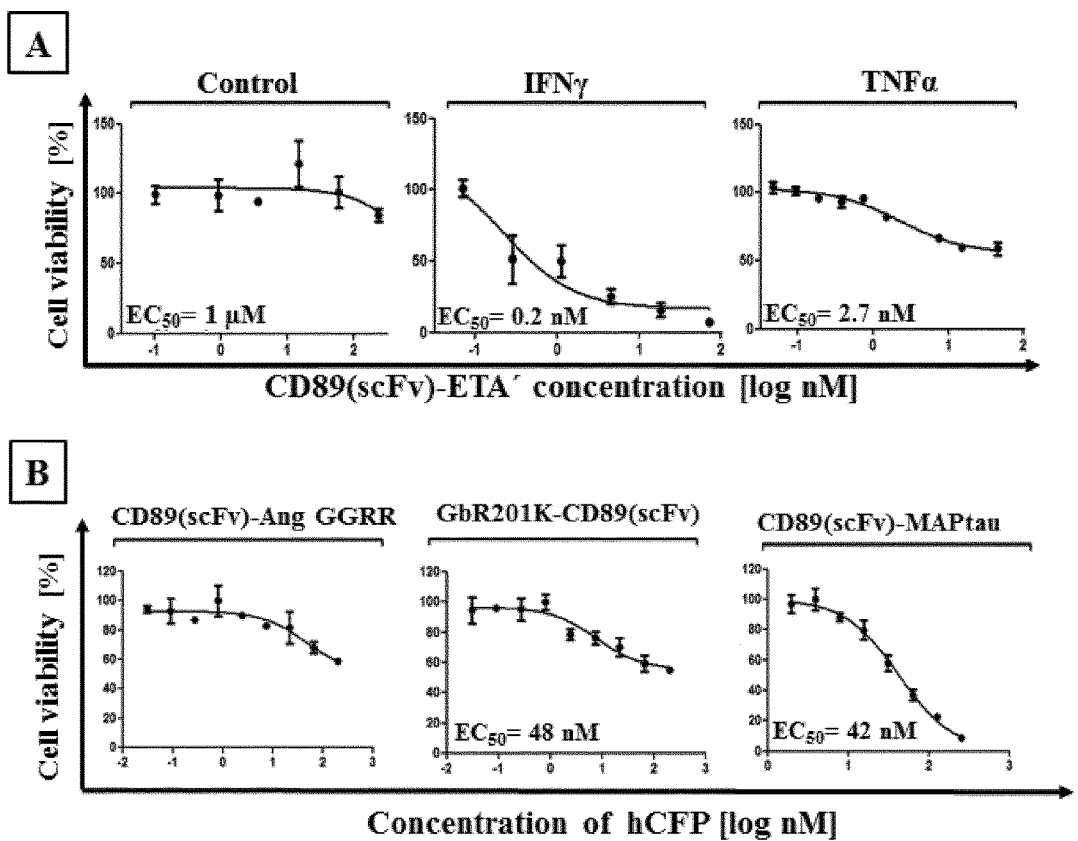
FIG. 8 (A) Cytotoxic effect of CD89(scFv)-ETA' against differently conditioned HL-60 cells measured with an XTT assay. (B) Cytotoxic effect of CD89(scFv)-Ang GGRR, GbR201K-CD89(scFv) and CD89(scFv)-MAPtau towards HL-60 cells (stimulated with 200 U/ml IFNγ) is obtained using XTT assay. Data represent mean values with standard deviations of triplicates.

In Vitro Inhibition of Cell Proliferation by CD89(scFv)-fusion Cytotoxic Proteins The EC50 value of CD89(scFv)-ETA' towards HL-60 cells was stimulus-dependent, i.e. it was >1 µM in the absence of stimuli, ~0.2 nM in the presence of IFNγ and ~3 nM in the presence of TNFα (FIG. 8 (A)). The inhibitory activity of cell proliferation by CD89(scFv)-ETA' was similar to that previously described for H22(scFv)-ETA' under comparable conditions (Barth S., et al., Blood 2000, 95: p. 3909-14; Barth S., et al., Applied and environmental microbiology, 2000, 66: p. 1572-9). The EC50 values calculated for stimulated HL-60 cells was ~47 nM for CD89(scFv)-Ang GGRR, ~42 nM for CD89(scFv)-MAPtau and ~48 nM for GbR201K-CD89(scFv) (FIG. 8 (B)).

8. Analysis of Internalisation

The CD89(scFv)-SNAP protein was produced by secretory expression in HEK293T cells, and coupled to BG-Vista® Green according to the manufacturer's instructions (NEB). Internalisation was verified by incubating $1 \times 10^6$ HL-60 (1000 U/mL TNFα) and Ramos cells with 50 nM (~2 µg) CD89(scFv)-SNAP-BG-Vista® Green in PBS at 4° C. or 37° C. for 30 min. After washing the cells twice, antigen-dependent internalisation was detected using a Leica TCS SP8 Confocal Microscope (Leica Microsystems).

CD89-dependent Internalisation

Efficient CD89-specific internalisation into HL60 cells was demonstrated using CD89(scFv)-SNAP-BG-Vista® Green, revealing the intracellular accumulation of the labelled protein after incubation for 30 min at 37° C. No internalisation was detected at 4° C. Neither binding nor internalisation was observed when we tested CD89 Ramos cells as a negative control (FIG. 9 (C)).

9. Statistical Analysis

Statistical analysis and $EC_{50}$ value calculations were carried our using GraphPad Prism v5 (GraphPad Software, USA). The $EC_{50}$ was defined as the concentration required to achieve 50% reduction of metabolic activity normalised to untreated control cells and zeocin-treated cells. Data were expressed as the mean±standard deviation (SD). Statistical comparisons were made using a two-tailed unpaired Student's t-test: *p 0.05, p 0.01, *p 0.001.

TABLE 1

Laboratory parameters of the three leukaemia patients

| PARAMETER | NUMBER | | |
|---|---|---|---|
| PATIENTS NUMBER | #1 | #2 | #3 |
| AGE | 59 | 91 | 47 |
| GENDER | MALE | FEMALE | FEMALE |
| WHO SUBTYPE | AML M5 | CMML-2 | CMML-2 |
| LABORATORY PARAMETERS | | | |
| WBC (G/L) | 12.4 | 105.7 | 76.7 |
| % MONOCYTES | 26 | 9 | 1 |
| HEMOGLOBIN (G/L) | 73 | 98 | 84 |
| PLATELET COUNT (G/L) | 11 | 64 | 118 |
| PREVIOUS TREATMENT | No | No | No |
| BIOMARKER PHENOTYPE | | | |
| CD64+ CD89+ | 74% | N.E.* | 73% |
| CD33+ CD89+ | 74% | N.E.* | 73% |
| CD89+ CELLS | 75% | 69% | 73% |

*Not Estimated (N.E.) for the particular patient.

Patient information (e.g. gender and age), diagnosis based on the WHO classification, state of previous treatment and general laboratory parameters (e.g. amount of the white blood cells (WBC) and monocyte percentage thereof, the hemoglobin amount, and platelet count) are filed in the table above according to the standard clinical protocols. Data is kindly provided by the corresponding member(s) in university clinic of Aachen according to the ethical policy.

REFERENCES

Albo, C., de la Fuente, J., Ares, C., Alonso, C. & Feteira, E. (2004) Kinetics and immunophenotypic characterization of circulating hematopoietic progenitor cells after peripheral blood stem cell transplantation. *Haematologica*, 89, 845-851.

Barth, S., Huhn, M., Matthey, B., Tawadros, S., Schnell, R., Schinkothe, T., Diehl, V. & Engert, A. (2000) Ki-4(scFv)-ETA', a new recombinant anti-CD30 immunotoxin with highly specific cytotoxic activity against disseminated Hodgkin tumors in SCID mice. *Blood*, 95, 3909-3914.

Becker, N. & Benhar, I. (2012) Antibody-Based Immunotoxins for the Treatment of Cancer. *Antibodies*, 1, 39-69.

Berges, N., Hehmann-Titt, G., Hristodorov, D., Melmer, G., Thepen, T. & Barth, S. (2014) Human Cytolytic Fusion Proteins: Modified Versions of Human Granzyme B and Angiogenin Have the Potential to Replace Bacterial Toxins in Targeted Therapies against CD64+ Diseases. *Antibodies*, 3, 92-115.

Chari, R. V. (2008) Targeted cancer therapy: conferring specificity to cytotoxic drugs. *Acc Chem Res*, 41, 98-107.

Cremer C., Vierbuchen T., Hein L., Fischer R., Barth S., Nachreiner T.—Angiogenin mutants as novel effector molecules for the generation of fusion proteins with increased cytotoxic potential, Journal of Immunotherapy. (accepted for publication, December 2014)

Dunphy, C. H. & Tang, W. (2007) The value of CD64 expression in distinguishing acute myeloid leukemia with monocytic differentiation from other subtypes of acute myeloid leukemia: a flow cytometric analysis of 64 cases. *Arch Pathol Lab Med*, 131, 748-754.

Gasiorowski, R. E., Clark, G. J., Bradstock, K. & Hart, D. N. (2014) Antibody therapy for acute myeloid leukaemia. *Br J Haematol*, 164, 481-495.

Goodin, S. (2007) Oral chemotherapeutic agents: understanding mechanisms of action and drug interactions. *Am J Health Syst Pharm*, 64, S15-24.

Guettinger, Y., Barbin, K., Peipp, M., Bruenke, J., Dechant, M., Horner, H., Thierschmidt, D., Valerius, T., Repp, R., Fey, G. H. & Stockmeyer, B. (2010) A recombinant bispecific single-chain fragment variable specific for HLA class II and Fc alpha RI (CD89) recruits polymorphonuclear neutrophils for efficient lysis of malignant B lymphoid cells. *J Immunol*, 184, 1210-1217.

Hamre, R., Farstad, I. N., Brandtzaeg, P. & Morton, H. C. (2003) Expression and modulation of the human immunoglobulin A Fc receptor (CD89) and the FcR gamma chain on myeloid cells in blood and tissue. *Scand J Immunol*, 57, 506-516.

Horner M J, R. L., Krapcho M, Neyman N (2009) Surveillance Epidemiology and End Results (SEER) "Cancer Statistics Review, 1975-2006". *National Cancer Institute*.

Hristodorov, D., Mladenov, R., Brehm, H., Fischer, R., Barth, S. & Thepen, T. (2014) Recombinant H22(scFv) blocks CD64 and prevents the capture of anti-TNF monoclonal antibody. *MAbs*, 6, 1283-1289.

Hristodorov, D., Mladenov, R., Huhn, M., Barth, S. & Thepen, T. (2012) Macrophage-targeted therapy: CD64-based immunotoxins for treatment of chronic inflammatory diseases. *Toxins*, 4, 676-694.

Hristodorov, D., R. Mladenov, A. Pardo, A. T. Pham, M. Huhn, R. Fischer, T. Thepen and S. Barth (2013). "Microtubule-associated protein tau facilitates the targeted killing of proliferating cancer cells in vitro and in a xenograft mouse tumour model in vivo." Br J Cancer 109(6): 1570-1578

Monnier, P., Vigouroux, R. & Tassew, N. (2013) In Vivo Applications of Single Chain Fv (Variable Domain) (scFv) Fragments. *Antibodies*, 2, 193-208.

Morton, H. C. & Brandtzaeg, P. (2001) CD89: the human myeloid IgA Fc receptor. *Arch Immunol Ther Exp (Warsz)*, 49, 217-229.

Paul, W E., Fundamental immunology, 1993, 3rd edition.

Potala, S., Sahoo, S. K. & Verma, R. S. (2008) Targeted therapy of cancer using diphtheria toxin-derived immunotoxins. *Drug Discov Today*, 13, 807-815.

Ribbert, T., Thepen, T., Tur, M. K., Fischer, R., Huhn, M. & Barth, S. (2010) Recombinant, ETA'-based CD64 immunotoxins: improved efficacy by increased valency, both in vitro and in vivo in a chronic cutaneous inflammation model in human CD64 transgenic mice. *Br J Dermatol*, 163, 279-286.

Roehm, N. W., Rodgers, G. H., Hatfield, S. M. & Glasebrook, A. L. (1991) An improved colorimetric assay for cell proliferation and viability utilizing the tetrazolium salt XTT. *J Immunol Methods*, 142, 257-265.

Schiffer, S., Letzian, S., Jost, E., Mladenov, R., Hristodorov, D., Huhn, M., Fischer, R., Barth, S. & Thepen, T. (2013) Granzyme M as a novel effector molecule for human cytolytic fusion proteins: CD64-specific cytotoxicity of Gm-H22(scFv) against leukemic cells. *Cancer Lett*, 341, 178-185.

Schiffer, S., Rosinke, R., Jost, E., Hehmann-Titt, G., Huhn, M., Melmer, G., Barth, S. & Thepen, T. (2014) Targeted ex vivo reduction of CD64-positive monocytes in chronic myelomonocytic leukemia and acute myelomonocytic leukemia using human granzyme B-based cytolytic fusion proteins. *Int J Cancer*, 135, 1497-1508.

Schwemmlein, M., Peipp, M., Barbin, K., Saul, D., Stockmeyer, B., Repp, R., Birkmann, J., Oduncu, F., Emmerich, B. & Fey, G. H. (2006) A CD33-specific single-chain immunotoxin mediates potent apoptosis of cultured human myeloid leukaemia cells. *Br J Haematol*, 133, 141-151.

Stahnke, B., Thepen, T., Stocker, M., Rosinke, R., Jost, E., Fischer, R., Tur, M. K. & Barth, S. (2008) Granzyme B-H22(scFv), a human immunotoxin targeting CD64 in acute myeloid leukemia of monocytic subtypes. *Mol Cancer Ther*, 7, 2924-2932.

Stanbury, R. M. & Graham, E. M. (1998) Systemic corticosteroid therapy—side effects and their management. *Br J Ophthalmol*, 82, 704-708.

Stein, C., Kellner, C., Kugler, M., Reiff, N., Mentz, K., Schwenkert, M., Stockmeyer, B., Mackensen, A. & Fey, G. H. (2010) Novel conjugates of single-chain Fv antibody fragments specific for stem cell antigen CD123 mediate potent death of acute myeloid leukaemia cells. *Br J Haematol*, 148, 879-889.

Stucker, F. & Ackermann, D. (2011) [Immunosuppressive drugs—how they work, their side effects and interactions]. *Ther Umsch*, 68, 679-686.

Thepen, T., Huhn, M., Melmer, G., Tur, M. K. & Barth, S. (2009) Fcgamma receptor 1 (CD64), a target beyond cancer. *Curr Pharm Des*, 15, 2712-2718.

Thepen, T., van Vuuren, A. J., Kiekens, R. C., Damen, C. A., Vooijs, W. C. & van De Winkel, J. G. (2000) Resolution of cutaneous inflammation after local elimination of macrophages. *Nat Biotechnol*, 18, 48-51.

Thorpe, S. J., Turner, C., Heath, A., Feavers, I., Vatn, I., Natvig, J. B. & Thompson, K. M. (2003) Clonal analysis of a human antimouse antibody (HAMA) response. *Scand J Immunol*, 57, 85-92.

Tur, M. K., Huhn, M., Thepen, T., Stocker, M., Krohn, R., Vogel, S., Jost, E., Osieka, R., van de Winkel, J. G., Fischer, R., Finnern, R. & Barth, S. (2003) Recombinant CD64-specific single chain immunotoxin exhibits specific cytotoxicity against acute myeloid leukemia cells. *Cancer Res*, 63, 8414-8419.

Vermes I, Haanen C, Steffens-Nakken H, Reutelingsperger C P. A novel assay for apoptosis. Flow cytometric detection of phosphatidylserine expression on early apoptotic cells using fluorescein labelled Annexin V. J Immunol Methods. 1995; 184:39-51

---

What is claimed is:

1. A complex suitable for targeting and killing a human target cell, the complex comprising a first polypeptide comprising a binding structure for binding the complex to a cellular surface receptor CD89 presented on the cell surface of said human target cell and a second polypeptide comprising a toxic effector domain, wherein the first polypeptide comprises the amino acid sequence of SEQ ID NO: 1.

2. The complex according to claim 1, wherein the binding structure is an antibody or an antibody fragment selected from the group consisting of an Fab, a scFv, a bis scFv, an Fab$_2$, an Fab$_3$, a minibody, a diabody, a triabody, a tetrabody and a tandab.

3. The complex according to claim 1, wherein the toxic effector domain is selected from the group consisting of a protease, a serine protease, granzyme B, granzyme A, granzyme H, granzyme K, granzyme M, a trypsin, a chymotrypsin, a bacteria-originated toxic compound, *Pseudomonas aeruginosa* exotoxin A (ETA), a human hydrolase, angiogenin, a cytoskeleton-associated protein, microtubule-associated protein tau, a photosensitizer, a plant-originated toxin, and Ricin A.

4. The complex according to claim 1, wherein the binding structure is a CD89-specific single-chain variable fragment (scFv) and the toxic effector domain is selected from the group consisting of *Pseudomonas aeruginosa* exotoxin A (ETA), granzyme B, angiogenin, and microtubule-associated protein tau.

5. A complex suitable for targeting and killing a human target cell, the complex comprising a first polypeptide comprising a binding structure for binding the complex to a cellular surface receptor CD89 presented on the cell surface of said human target cell and a second polypeptide comprising a toxic effector domain, wherein the complex comprises an amino acid sequence selected from the group consisting of SEQ ID NO: 2, SEQ ID NO: 3, SEQ ID NO: 4 and SEQ ID NO: 5.

6. The complex according to claim 1, wherein the human target cell is a cancer cell.

7. An isolated nucleic acid molecule encoding the complex according to claim 1.

8. A vector comprising the nucleic acid molecule of claim 7.

9. A host cell transformed with the vector of claim 8.

10. A pharmaceutical composition comprising a complex according to claim 1 in combination with a pharmacologically acceptable carrier, diluent, stabilizer or formulation.

11. A method for preparing a complex suitable for targeting and killing a human target cell, the complex comprising a first polypeptide comprising a binding structure for binding the complex to a cellular surface receptor CD89 presented on the cell surface of said human target cell and a second polypeptide comprising a toxic effector domain, the method comprising culturing the host cell according to claim 10 and isolating the complex from the cultured host cell.

12. A method for the treatment of a disease selected from the group consisting of a malignant disease, a chronic inflammatory disease, a cutaneous disease, an autoimmune disease, and an intestinal disease, the method comprising administering an effective amount of the pharmaceutical of claim 10 to a patient in need thereof, wherein:
  the malignant disease or chronic inflammatory disease is selected from the group consisting of acute myeloid leukaemia, arthritis, chronic obstructive pulmonary disease (COPD), emphysema, intrinsic asthma, and extrinsic asthma;
  the cutaneous disease is selected from the group consisting of atopic dermatitis, psoriasis, polymorphic light eruption, and systemic lupus erythematosus (SLE);
  the autoimmune disease is selected from the group consisting of graft versus host, multiple sclerosis, macrophage activation syndrome, rheumatoid arthritis, juvenile arthritis;
  the intestinal disease is Crohn's disease or chronic bowel disease.

13. The method according to claim 12, wherein the disease is myeloid leukaemia.

14. A method of treating a malignant disease, autoimmune disease, tissue rejection reaction, or chronic inflammatory disease comprising administering an effective amount of the complex according to claim 1 to a patient in need thereof.

15. A polypeptide suitable for the detection of CD89, wherein said polypeptide comprises the amino acid sequence of SEQ ID NO: 1.

16. The polypeptide according to claim 15, wherein said polypeptide is coupled to a detectable label.

17. The polypeptide according to claim 15, wherein the CD89 is presented on a human target cell or a fragment thereof.

18. A method of detecting the presence of CD89 or a cell expressing CD89 in a sample, comprising: contacting the sample with a polypeptide according to claim 15 under conditions that allow for formation of a complex between the polypeptide and CD89; and detecting the formation of the complex.

19. A method for the detection of CD89 contained in a sample, the method comprising:
  (a) contacting a sample with a polypeptide according to claim 15 and with a fusion tag specific fluorophore that specifically binds the fusion tag coupled to said polypeptide; and
  (b) detecting the presence of CD89 in the sample by fluorescence signals associated with the fusion tag specific fluorophore.

20. A method for the diagnosis of CD89+ malignancies, comprising contacting a biological sample taken from a patient with a polypeptide according to claim 15.

* * * * *